United States Patent
Minich et al.

(10) Patent No.: US 6,894,067 B2
(45) Date of Patent: May 17, 2005

(54) 5-HETEROATOM-SUBSTITUTED PYRAZOLES

(75) Inventors: Martha L. Minich, Gales Ferry, CT (US); Subas M. Sakya, East Lyme, CT (US); Andrei Shavnya, East Lyme, CT (US); Kristin Lundy DeMello, Ledyard, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/285,744

(22) Filed: Nov. 1, 2002

(65) Prior Publication Data

US 2003/0134858 A1 Jul. 17, 2003

Related U.S. Application Data

(60) Provisional application No. 60/335,733, filed on Nov. 2, 2001.

(51) Int. Cl.$^7$ .................. C07D 401/04; C07D 401/14; A61K 31/4427; A61P 19/02; A61P 35/00
(52) U.S. Cl. .................. 514/352; 546/275.4; 544/326; 544/331
(58) Field of Search ............. 546/275.4; 514/352

(56) References Cited

FOREIGN PATENT DOCUMENTS

| | | | |
|---|---|---|---|
| EP | 1104758 | 6/2001 | ......... C07D/401/04 |
| EP | 1104759 | 6/2001 | ......... C07D/405/14 |
| EP | 1104760 | 6/2001 | ......... C07D/405/14 |
| EP | 1142889 | 10/2001 | ......... C07D/401/04 |
| WO | WO9711704 | 4/1997 | ......... A61K/31/635 |
| WO | WO0140216 | 6/2001 | ......... C07D/401/04 |
| WO | WO0164669 | 9/2001 | ......... C07D/401/04 |

OTHER PUBLICATIONS

McMurray et al. Am. J. Med. Sci. 323(4): 181–189, 2002.*
Vane, J.R., et al., *Proc. Natl. Acad. Sci. USA*, 1994, 91, 2046.
U.S. Appl. No. 09/798,752, filed Mar. 2, 2001 (our reference: PC10826A).
U.S. Appl. No. 09/824,550, filed Apr. 2, 2001 (our reference: PC10809A).
U.S. Appl. No. 60/335,713, filed Nov. 2, 2001 (our reference: PC23183).
U.S. Appl. No. 60/335,736, filed Nov. 2, 2001 (our reference: PC23185).
U.S. Appl. No. 60/335,738, filed Nov. 2, 2001 (our reference: PC23166).
U.S. Appl. No. 60/336,306, filed Nov. 2, 2001 (our reference: PC23181).

* cited by examiner

*Primary Examiner*—Venkataraman Balasubramanian
(74) *Attorney, Agent, or Firm*—Mary J. Hosley; Timothy B. Creagan; Peter Richardson

(57) ABSTRACT

The present invention relates to 5-heteroatom-substituted pyrazoles of the formula I:

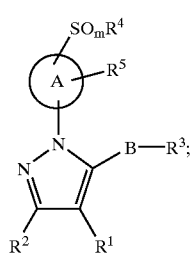

wherein the ring of the formula $(R^5)$-A-$(SO_mR^4)$, m, B, $R^1$ through $R^5$ are as defined in the specification, to pharmaceutical compositions containing them and to their medicinal use. The compounds of the invention are useful in the treatment or alleviation of inflammation and other inflammation associated disorders, such as arthritis, colon cancer, and Alzheimer's disease in mammals, preferably humans, dogs, cats and livestock animals.

13 Claims, No Drawings

5-HETEROATOM-SUBSTITUTED PYRAZOLES

CROSS-REFERENCE TO RELATED APPLICATION

This application claims benefit of U.S. provisional application No. 60/335,733, filed Nov. 2, 2001.

BACKGROUND OF THE INVENTION

This invention relates to 5-heteroatom-substituted pyrazoles, methods of treatment and pharmaceutical compositions for the treatment of cyclooxygenase mediated diseases, such as arthritis, neurodegeneration and colon cancer, in mammals, preferably humans, dogs, cats or livestock.

Sulfonyl pyrazoles are useful in the treatment of cyclooxygenase (COX) mediated diseases, such as arthritis, neurodegeneration and colon cancer, in mammals, preferably humans, dogs, cats or livestock. Two forms of COX are now known, a constitutive isoform (COX-1) and an inducible isoform (COX-2) of which expression is upregulated at sites of inflammation (Vane, J. R.; Mitchell, et. al., *Proc. Natl. Acad. Sci. USA*, 1994, 91, 2046). COX-1 appears to play a physiological role and to be responsible for gastrointestinal and renal protection. On the other hand, COX-2 appears to play a pathological role and is believed to be the predominant isoform present in inflammation conditions. The therapeutic use of conventional COX inhibitors are limited due to drug associated side effects, including life threatening ulceration and renal toxicity. Compounds that selectively inhibit COX-2 would exert anti-inflammatory effects without the adverse side effects associated with COX-1 inhibition. Preferred compounds of the invention are selective COX-2 inhibitors.

A variety of sulfonylpyrazoles that inhibit COX have been described in patent publications WO 97/11704, WO 01/40216, EP 1104758, EP 1104759, and EP 1104760; U.S. Non-Provisional patent application Ser. No. 09/798,752, filed Mar. 2, 2001; and U.S. Non-Provisional patent application Ser. No. 09/824,550, filed Apr. 2, 2001.

Filed simultaneously with the present application on Nov. 2, 2001, are United States Provisional Applications entitled "Hydrazinyl and Nitrogen Oxide Pyrazoles"; "Heterocyclo-Alkylsulfonyl Pyrazoles"; "5-Heterocyclo-Pyrazoles"; and "5-(Alkylidene-Cycloalkyl)- and 5-(Alkylidene-Heterocyclyl)-Pyrazoles", which refer to certain pyrazole COX-2 inhibitors. The aforesaid applications are herein incorporated in their entireties by reference.

SUMMARY OF THE INVENTION

The present invention relates to a compound of the formula I:

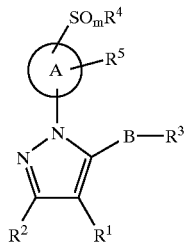

I or the pharmaceutically acceptable salts thereof;

wherein the ring of the formula $(R^5)$-A-$(SO_mR^4)$ is selected from the group consisting of

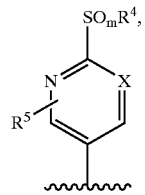

A1

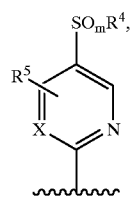

A2

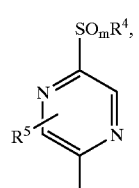

A3

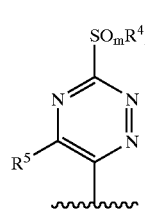

A4

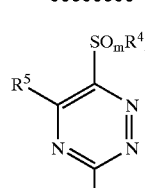

A5

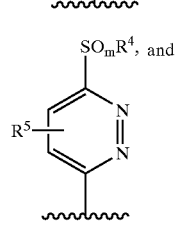

A6

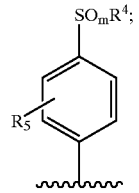

A7 m is 0, 1 or 2;
X is >CR$^5$ or >N;
R$^1$ is a radical selected from the group consisting of H, —NO$_2$, —CN, (C$_1$-C$_6$)alkyl, (C$_1$-C$_6$)alkyl-SO$_2$—, (C$_6$-C$_{10}$)aryl-SO$_2$—, H—(C=O)—, (C$_1$-C$_6$)alkyl-(C=O)—, (C$_1$-C$_6$)alkyl-O—(C=O)—, C$_1$-C$_9$) heteroaryl-(C=O)—, (C$_1$-C$_9$)heterocyclyl-(C=O)—, $H_2N$—(C=O)—, $(C_1$-$C_6)$alkyl-NH—(C=O)—, [$(C_1$-$C_6)$alkyl]$_2$—NH—(C=O)—, [$(C_6$-$C_{10})$aryl]-NH—(C=O)—, [$(C_1$-$C_6)$alkyl]-[$((C_6$-$C_{10})$aryl)-N]—NH—(C=O)—, HO—HN—(C=O)—, or $(C_1$-$C_6)$alkyl-O—NH—(C=O)—;

$R^2$ is a radical selected from the group consisting of H, —$NO_2$, —CN, $(C_2$-$C_6)$alkenyl, $(C_2$-$C_6)$alkynyl, $(C_3$-$C_7)$cycloalkyl, $(C_6$-$C_{10})$aryl, $(C_1$-$C_9)$heteroaryl, $(C_1$-$C_9)$heterocyclyl, $(C_1$-$C_6)$alkyl-O—, $(C_3$-$C_7)$cycloalkyl-O—, $(C_6$-$C_{10})$aryl-O—, $(C_1$-$C_9)$heteroaryl-O—, $(C_1$-$C_9)$heterocyclyl-O—, H—(C=O)—, $(C_1$-$C_6)$alkyl-(C=O)—, $(C_3$-$C_7)$cycloalkyl-(C=O)—, $(C_6$-$C_{10})$aryl-(C=O)—, $(C_1$-$C_9)$heteroaryl-(C=O)—, $(C_1$-$C_9)$heterocyclyl-(C=O)—, $(C_1$-$C_6)$alkyl-O—(C=O)—, $(C_3$-$C_7)$cycloalkyl-O—(C=O)—, $(C_6$-$C_{10})$aryl-O—(C=O)—, $(C_1$-$C_9)$heteroaryl-O—(C=O)—, $(C_1$-$C_9)$heterocyclyl-O—(C=O)—, $(C_1$-$C_6)$alkyl-(C=O)—O—, $(C_3$-$C_7)$cycloalkyl-(C=O)—O—, $(C_6$-$C_{10})$aryl-(C=O)—O—, $(C_1$-$C_9)$heteroaryl-(C=O)—O—, $(C_1$-$C_9)$heterocyclyl-(C=O)—O—, $(C_1$-$C_6)$alkyl-(C=O)—NH—, $(C_3$-$C_7)$cycloalkyl-(C=O)—NH—, $(C_6$-$C_{10})$aryl-(C=O)—NH—, $(C_1$-$C_9)$heteroaryl-(C=O)—NH—, $(C_1$-$C_9)$heterocyclyl-(C=O)—NH—, $(C_1$-$C_6)$alkyl-O—(C=O)—NH—, $(C_1$-$C_6)$alkyl-NH—, [$(C_1$-$C_6)$alkyl]$_2$—N—, $(C_3$-$C_7)$cycloalkyl-NH—, [$(C_3$-$C_7)$cycloalkyl]$_2$—N—, [$(C_6$-$C_{10})$aryl]-NH—, [$(C_6$-$C_{10})$aryl]$_2$—N—, [$(C_1$-$C_6)$alkyl]-[$((C_6$-$C_{10})$aryl)-N]—, [$(C_1$-$C_9)$heteroaryl]-NH—, [$(C_1$-$C_9)$heteroaryl]$_2$—N—, [$(C_1$-$C_9)$heterocyclyl]-NH—, [$(C_1$-$C_9)$heterocyclyl]$_2$—N—, $H_2N$—(C=O)—, HO—NH—(C=O)—, $(C_1$-$C_6)$alkyl-O—NH—(C=O)—, [$(C_1$-$C_6)$alkyl]-NH—(C=O)—, [$(C_1$-$C_6)$alkyl]$_2$—NH—(C=O)—, [$(C_3$-$C_7)$cycloalkyl]-NH—(C=O)—, [$(C_3$-$C_7)$cycloalkyl]$_2$—NH—(C=O)—, [$(C_6$-$C_{10})$aryl]-NH—(C=O)—, [$(C_6$-$C_{10})$aryl]$_2$—NH—(C=O)—, [$(C_1$-$C_6)$alkyl]-[$((C_6$-$C_{10})$aryl)-N]—(C=O)—, [$(C_1$-$C_9)$heteroaryl]-NH—(C=O)—, [$(C_1$-$C_9)$heteroaryl]$_2$—NH—(C=O)—, [$(C_1$-$C_9)$heterocyclyl]-NH—(C=O)—, $(C_1$-$C_6)$alkyl-S—, and $(C_1$-$C_6)$alkyl optionally substituted by one —OH substituent or by one to four fluoro substituents;

B is —O—, —S—, —SO—, —$SO_2$— or $R^6$—N—;

$R^3$ is a radical selected from the group consisting of $(C_1$-$C_6)$alkyl, $(C_6$-$C_{10})$aryl, $(C_3$-$C_{10})$cycloalkyl, $(C_1$-$C_9)$heteroaryl and $(C_1$-$C_9)$heterocyclyl;

wherein each of said $R^3$ $(C_1$-$C_6)$alkyl, $(C_6$-$C_{10})$aryl, $(C_3$-$C_{10})$cycloalkyl, $(C_1$-$C_9)$heteroaryl or $(C_1$-$C_9)$heterocyclyl radicals may optionally be substituted with one to three substituents independently selected from the group consisting of halo, —$NH_2$, —OH, —CN, —$NO_2$, —$OCF_3$, —$CF_3$, $(C_1$-$C_6)$alkyl, $(C_2$-$C_6)$alkenyl, $(C_2$-$C_6)$alkynyl, $(C_6$-$C_{10})$aryl, $(C_3$-$C_{10})$cycloalkyl, $(C_1$-$C_9)$heteroaryl, $(C_1$-$C_9)$heterocyclyl, $(C_1$-$C_6)$alkyl-O—, $(C_3$-$C_{10})$cycloalkyl-O—, $(C_6$-$C_{10})$aryl-O—, $(C_1$-$C_9)$heteroaryl-O—, and $(C_1$-$C_9)$heterocyclyl-O—;

wherein each of said $R^3$ $(C_1$-$C_6)$alkyl, $(C_6$-$C_{10})$aryl, $(C_3$-$C_{10})$cycloalkyl, $(C_1$-$C_9)$heterocyclyl or $(C_1$-$C_9)$heteroaryl substituents may optionally be substituted with one to three moieties independently selected from the group consisting of halo, —$NH_2$, HO—, $(C_1$-$C_6)$alkyl-O—, $(C_1$-$C_6)$alkyl, $(C_2$-$C_6)$alkenyl, $(C_2$-$C_6)$alkynyl-CN, —$NO_2$, —$OCF_3$, and —$CF_3$;

wherein each of said —$NH_2$ substituents may optionally be substituted by one to two moieties independently selected from the group consisting of $(C_1$-$C_6)$alkyl, $(C_6$-$C_{10})$aryl, $(C_3$-$C_{10})$cycloalkyl, $(C_1$-$C_9)$heterocyclyl and $(C_1$-$C_9)$heteroaryl, wherein said moieties are optionally substituted by one or two sub-moieties independently selected from the group consisting of halo, —$NH_2$, HO—, $(C_1$-$C_6)$alkyl-O—, $(C_1$-$C_6)$alkyl, —$OCF_3$ and —$CF_3$;

$R^4$ is a radical selected from the group consisting of $(C_1$-$C_6)$alkyl-NH—, [$(C_1$-$C_6)$alkyl]$_2$—N—, $(C_3$-$C_7)$cycloalkyl-NH—, $(C_6$-$C_{10})$aryl-NH—, $(C_1$-$C_9)$heteroaryl-NH—, $(C_1$-$C_6)$alkyl-(C=O)—NH—, $(C_3$-$C_7)$cycloalkyl-(C=O)—NH—, $(C_6$-$C_{10})$aryl-(C=O)—NH—, $(C_1$-$C_9)$heteroaryl-(C=O)—NH—, $(C_1$-$C_6)$alkyl-O—(C=O)—NH—, $(C_3$-$C_7)$cycloalkyl-O—(C=O)—NH—, $(C_6$-$C_{10})$aryl-O—(C=O)—NH—, $(C_1$-$C_9)$heteroaryl-O—(C=O)—NH—, $(C_1$-$C_6)$alkyl-NH—(C=O)—NH—, [$(C_1$-$C_6)$alkyl]$_2$—NH—(C=O)—NH—, $(C_3$-$C_7)$cycloalkyl-NH—(C=O)—NH—, $(C_6$-$C_{10})$aryl-NH—(C=O)—NH—, $(C_1$-$C_9)$heteoaryl]-NH—(C=O)—NH—, $(C_1$-$C_6)$alkyl-NH—HC=N—, [$C_1$-$C_6)$alkyl]$_2$N—HC=N—, and $(C_6$-$C_{10})$aryl-NH—HC=N—;

$R^5$ is a radical selected from the group consisting of H, halo, —OH, $(C_1$-$C_6)$alkyl-O—, $(C_2$-$C_6)$alkenyl, $(C_2$-$C_6)$alkynyl, $(C_3$-$C_7)$cycloalkyl, —CN, H—(C=O)—, $(C_1$-$C_6)$alkyl-(C=O)—, $(C_1$-$C_6)$alkyl-(C=O)—O—, HO—(C=O)—, $(C_1$-$C_6)$alkyl-O—(C=O)—, $(C_1$-$C_6)$alkyl-NH—, [$(C_1$-$C_6)$alkyl]$_2$—N—, $(C_3$-$C_7)$cycloalkyl-NH—, $(C_6$-$C_{10})$aryl-NH—, [$(C_1$-$C_6)$alkyl]-[$((C_6$-$C_{10})$aryl)-N]—, $(C_1$-$C_9)$heteroaryl-NH—, $H_2N$—(C=O)—, $(C_1$-$C_6)$alkyl-NH—(C=O)—, [$(C_1$-$C_6)$alkyl]$_2$—NH—(C=O)—, $(C_6$-$C_{10})$aryl-(C=O)—, [$(C_1$-$C_6)$alkyl]-[$((C_6$-$C_{10})$aryl)-N]—(C=O)—, $(C_1$-$C_6)$alkyl-O—NH—(C=O)—, $(C_1$-$C_6)$alkyl-S—, and $(C_1$-$C_6)$alkyl optionally substituted with one to four fluoro atoms; and $R^6$ is a radical selected from the group consisting of H, $(C_1$-$C_6)$alkyl, $(C_6$-$C_{10})$aryl, $(C_3$-$C_{10})$cycloalkyl, $(C_1$-$C_9)$heteroaryl and $(C_1$-$C_9)$heterocyclyl.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, para-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines.

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds of the invention also exist in different tautomeric forms. This invention relates to all tautomers of formula I.

The compounds of this invention may contain olefin-like double bonds. When such bonds are present, the compounds of the invention exist as cis and trans configurations and as mixtures thereof.

The compounds of this invention may contain olefin-like double bonds. When such bonds are present, the compounds of the invention exist as cis and trans configurations and as mixtures thereof. Unless otherwise indicated, the term "functional group" refers to "radical", "substituent" "moiety", or "sub-moiety", as defined below. The term "sub-functional group" refers to "substituent" "moiety", or "sub-moiety", as defined below.

Unless otherwise indicated, the term "radical" or "radicals" refers to an individual member of a variable ($R^1$, $R^2$, $R^3$ etc) of the compound of the formula I (e.g., $R^1$ is a radical selected from the group consisting of H and ($C_1$–$C_6$)alkyl means that $R^1$ can be either a H radical or a ($C_1$–$C_6$)alkyl radical).

Unless otherwise indicated, the term "substituent" or "substituents" refers to a replacement of at least one atom of a radical, wherein the term "radical" is as defined above, by another atom or group of atoms. For example, an ($C_1$–$C_6$) alkyl substituent may replace a hydrogen atom of $R^1$ ($C_6$–$C_{10}$)aryl radical.

Unless otherwise indicated, the term "moiety" or "moieties" refers to a replacement of at least one atom of a substituent, wherein the term "substituent" is as defined above, by another atom or group of atoms. For example, an ($C_1$–$C_6$)alkyl moiety of a particular substituent (e.g., ($C_1$–$C_6$)alkyl, ($C_6$–$C_{10}$)aryl, or ($C_3$–$C_8$)cycloalkyl substituent) may replace a hydrogen atom of that substituent.

Unless otherwise indicated, the term "sub-moiety" or "sub-moieties" refers to a replacement of at least one atom of a moiety, wherein the term "moiety" is as defined above, by another atom or group of atoms. For example, an ($C_1$–$C_6$) alkyl sub-moiety of a particular moiety (e.g., ($C_1$–$C_6$)alkyl, ($C_6$–$C_{10}$)aryl, or ($C_3$–$C_8$)cycloalkyl moiety) may replace a hydrogen atom of that moiety.

Unless otherwise indicated, the term "($C_1$–$C_6$)alkyl" as well as the ($C_1$–$C_6$)alkyl component of other terms referred to herein (e.g., the "($C_1$–$C_6$)alkyl component of ($C_1$–$C_6$) alkyl-O—), may be linear or branched (such as methyl, ethyl, n-propyl, isopropyl, n-butyl, iso-butyl, secondary-butyl, tertiary-butyl), wherein each of said ($C_1$–$C_6$)alkyl functional group, wherever they occur, may optionally be substituted by one to three sub-functional groups per ($C_1$–$C_6$)alkyl component independently selected from the group consisting of fluoro, —OH, ($C_2$–$C_6$)alkenyl, ($C_2$–$C_6$) alkynyl, ($C_3$–$C_7$)cycloalkyl, ($C_1$–$C_6$)alkyl-O—, oxo, H—(C=O)—, $H_2$N—(C=O)—, ($C_1$–$C_6$)alkyl-(C=O)—, —CN, —$NO_2$, ($C_1$–$C_6$)alkyl-O—(C=O)—, ($C_1$–$C_6$)alkyl-NH—, [($C_1$–$C_6$)alkyl]$_2$—N—, ($C_3$–$C_7$)cycloalkyl-NH—, ($C_6$–$C_{10}$)aryl-NH—, [($C_1$–$C_6$)alkyl]-[(($C_6$–$C_{10}$)aryl)-N]—, ($C_1$–$C_9$)heteroaryl-NH—, ($C_1$–$C_{10}$)heterocyclyl-NH—, $H_2$N—(C=O)—, [($C_1$–$C_6$)alkyl]-NH—(C=O)—, [($C_1$–$C_6$)alkyl]$_2$—N—(C=O)—, [($C_6$–$C_{10}$)aryl]-NH—(C=O)—, [($C_1$–$C_6$)alkyl]-[(($C_6$–$C_{10}$)aryl)-N]—(C=O)—, ($C_1$–$C_6$)alkyl-O—NH—(C=O)—, ($C_6$–$C_{10}$)aryl, ($C_2$–$C_9$) heteroaryl, ($C_6$–$C_{10}$)aryl-O—, ($C_1$–$C_9$)heteroaryl-O—, ($C_1$–$C_9$)heteroaryl-(C=O)—, ($C_1$–$C_6$)alkyl-S—, ($C_1$–$C_6$) alkyl-S(=O)—, ($C_1$–$C_6$)alkyl-$SO_2$—, ($C_1$–$C_6$)alkyl-(C=O)—NH—, ($C_1$–$C_6$)alkyl-(C=O)—NH—($C_1$–$C_6$) alkyl-NH and ($C_1$–$C_6$)alkyl-(C=O)—O—.

Unless otherwise indicated, the term "halo" means fluoro, chloro, bromo or iodo.

Unless otherwise indicated, the term "($C_2$–$C_6$)alkenyl" means straight or branched hydrocarbon chain functional groups of 2 to 6 carbon atoms having at least one double bond including, but not limited to ethenyl, 1-propenyl, 2-propenyl (allyl), iso-propenyl, 2-methyl-1-propenyl, 1-butenyl, or 2-butenyl.

Unless otherwise indicated, the term "($C_2$–$C_6$)alkynyl" is used herein to mean straight or branched hydrocarbon chain functional groups of 2 to 6 carbon atoms having one triple bond including, but not limited to, ethynyl (—C≡C—H), propynyl (—$CH_2$—C≡C—H or —C≡C—$CH_3$), or butynyl (—$CH_2$—$CH_2$—C≡C—H, or —$CH_2$—C≡C—$CH_3$, or —C≡C—$CH_2CH_3$).

Unless otherwisse indicated, the term "($C_3$–$C_7$) cycloalkyl" refers to a mono or bicyclic carbocyclic ring functional groups including, but not limited to, cyclopropyl, cyclobutyl, cyclopentyl, cyclohexyl, cycloheptyl, cyclooctyl, cyclononyl, bicyclo[2.2.1]heptanyl, bicyclo[3.2.1]octanyl and bicyclo[5.2.0]nonanyl; wherein said ($C_3$–$C_7$)cycloalkyl may optionally contain 1 or 2 double bonds including, but not limited to, cyclopentenyl, cyclohexenyl and cycloheptenyl.

Unless otherwise indicated, the term "($C_6$–$C_{10}$)aryl" means aromatic functional groups such as phenyl, naphthyl, tetrahydronaphthyl, or indanyl, wherein said ($C_6$–$C_{10}$)aryl is optionally substituted on any ring carbon atom by one to two sub-functional groups per ring, wherein said sub-functional groups are independently selected from the group consisting of halo, —OH, —CN, —SH, HO—(C=O)—, —$NO_2$, ($C_1$–$C_6$)alkyl, ($C_2$–$C_6$)alkenyl, ($C_2$–$C_6$)alkynyl, ($C_3$–$C_7$) cycloalkyl, ($C_6$–$C_{10}$)aryl, ($C_1$–$C_9$)heteroaryl, ($C_1$–$C_9$) heterocyclyl, ($C_1$–$C_6$)alkyl-O—, —$OCF_3$, ($C_1$–$C_6$)alkyl-S—, ($C_1$–$C_6$)alkyl-NH—, [($C_1$–$C_6$)alkyl]$_2$—N—, ($C_3$–$C_7$) cycloalkyl-NH—, ($C_6$–$C_{10}$)aryl-NH—, [($C_1$–$C_6$)alkyl]-[(($C_6$–$C_{10}$)aryl)-N]—, ($C_1$–$C_9$)heteroaryl-NH—, ($C_1$–$C_{10}$) heterocyclyl-NH—, $H_2$N—(C=O)—, [($C_1$–$C_6$)alkyl]-NH—(C=O)—, [($C_1$–$C_6$)alkyl]$_2$—N—(C=O)—, [($C_6$–$C_{10}$)aryl]-NH—(C=O)—, [($C_1$–$C_6$)alkyl]-[(($C_6$–$C_{10}$) aryl)-N]—(C=O)—, ($C_1$–$C_6$)alkyl-O—NH—(C=O)—, ($C_1$–$C_6$)alkyl-(C=O)—O—, ($C_1$–$C_6$)alkyl-(C=O)—NH—($C_1$–$C_6$)alkyl-(C=O)—HN—($C_1$–$C_6$)alkyl-NH, H—(C=O)—, ($C_1$–$C_6$)alkyl-(C=O)— and ($C_1$–$C_6$)alkyl-O—(C=O)—.

Unless otherwise indicated, the term "[($C_1$–$C_6$)alkyl]-[(($C_6$–$C_{10}$)aryl)-N]—" has the following structure:

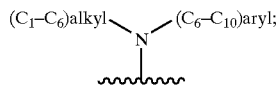

wherein the term "($C_1$–$C_6$)alkyl" and the term "($C_6$–$C_{10}$) aryl" are as defined above.

Unless otherwise indicated, the term "[($C_1$–$C_6$)alkyl]-[(($C_6$–$C_{10}$)aryl)-N]—(C=O)—" has the following structure:

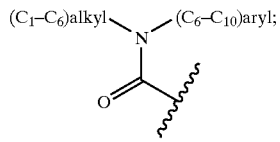

wherein the term "($C_1$–$C_6$)alkyl" and the term "($C_6$–$C_{10}$) aryl" are as defined above.

Unless otherwise indicated, the term "oxo" refers to =O.
Unless otherwise indicated, the term "[(C$_1$–C$_6$)alkyl]-NH—HC=N—" refers to

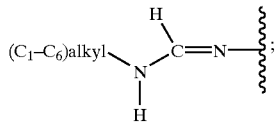

wherein the term "(C$_1$–C$_6$)alkyl" is as defined above.
Unless otherwise indicated, the term "[C$_1$–C$_6$)alkyl]$_2$N—HC=N—" refers to

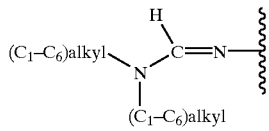

wherein the term "(C$_1$–C$_6$)alkyl" is as defined above.
Unless otherwise indicated, the term "[(C$_6$–C$_{10}$)aryl]-NH—HC=N—" refers to

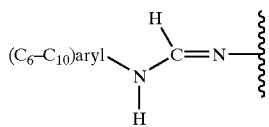

wherein the term "(C$_6$–C$_{10}$)aryl" is as defined above.

Unless otherwise indicated, the term "(C$_1$–C$_9$)heteroaryl" refers to aromatic or multicyclic functional groups wherein at least one ring of the functional groups is aromatic, wherein said aromatic or multicyclic functional groups contain one or more heteroatoms selected from the group consisting of O, S and N. The (C$_1$–C$_9$)heteroaryl functional groups can also be optionally substituted by one or more oxo sub-functional groups. Examples of heteroaryl functional groups include, but are not limited to, benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl, wherein said (C$_1$–C$_{10}$)heteroaryl is optionally substituted on any atoms capable of forming an additional bond by one or two sub-functional groups independently selected from halo, —CN, —OH, (C$_1$–C$_6$)alkyl, perfluoro(C$_1$–C$_6$)alkyl, perfluoro(C$_1$–C$_6$)alkyl-O—, (C$_1$–C$_6$)alkyl-O— and (C$_3$–C$_8$)cycloalkyl-O—. Unless otherwise indicated, the foregoing (C$_1$–C$_9$)heteroaryls functional groups can be C-attached or N-attached where such is possible. For instance, pyrrolyl can be pyrrol-1-yl (N-attached) or pyrrol-3-yl (C-attached).

Unless otherwise indicated, the term "(C$_1$–C$_9$)heterocyclyl" refers to a cyclic functional groups containing 1 to 9 carbon atoms and 1 to 4 heteroatoms selected from the group consisting of N, O and S. The heterocyclyl ring functional groups can also be optionally substituted where such is possible by oxo, —CN, —OH, (C$_1$–C$_6$)alkyl, perfluoro(C$_1$–C$_6$)alkyl, perfluoro(C$_1$–C$_6$)alkyl-O—, (C$_1$–C$_6$)alkyl-O— and (C$_3$–C$_8$)cycloalkyl-O—. Examples of the cyclic functional groups include, but not limited to, 3-azabicyclo[3.1.0]hexanyl, 3-azabicyclo[4.1.0]-heptanyl, azetidinyl, dihydrofuranyl, dihydropyranyl, dihydrothienyl, dioxanyl, 1,3-dioxolanyl, 1,4-dithianyl, hexahydroazepinyl, hexahydropyrimidine, imidazolidinyl, imidazolinyl, isoxazolidinyl, morpholinyl, oxazolidinyl, piperazinyl, piperidinyl, 2H-pyranyl, 4H-pyranyl, pyrazolidinyl, pyrazolinyl, pyrrolidinyl, 2-pyrrolinyl, 3-pyrrolinyl, quinolizinyl, tetrahydrofuranyl, tetrahydropyranyl, 1,2,3,6-tetrahydropyridinyl, tetrahydrothienyl, tetrahydrothiopyranyl, thiomorpholinyl, thioxanyl or trithianyl. Unless otherwise indicated, the foregoing heterocyclyl can be C-attached or N-attached where such is possible. For example, piperidinyl can be piperidin-1-yl (N-attached) or piperidin-4-yl (C-attached).

In one embodiment of the invention, R$^4$ is a radical selected from the group consisting of (C$_1$–C$_6$)alkyl-NH—, [(C$_1$–C$_6$)alkyl]$_2$—N—, (C$_3$–C$_7$)cycloalkyl-NH—, (C$_6$–C$_{10}$)aryl-NH—, (C$_1$–C$_9$)heteroaryl-NH—; preferably selected from the group consisting of (C$_1$–C$_6$)alkyl-NH— and (C$_3$–C$_7$)cycloalkyl-NH—; more preferably selected from the group consisting of methyl-NH—, ethyl-NH, cyclopropyl-NH—, cyclopentyl-NH—, and cyclohexyl-NH—.

In another embodiment of the invention, R$^4$ is a radical selected from the group consisting of (C$_1$–C$_6$)alkyl-(C=O)—NH—, (C$_3$–C$_7$)cycloalkyl-(C=O)—NH—, (C$_6$–C$_{10}$)aryl-(C=O)—NH—, and (C$_1$–C$_9$)heteroaryl-(C=O)—NH—; preferably selected from the group consisting of (C$_1$–C$_6$)alkyl-(C=O)—NH— and (C$_6$–C$_{10}$)aryl-(C=O)—NH—; preferably phenyl-(C=O)—NH—.

In another embodiment of the invention, R$^4$ is a radical selected from the group consisting of (C$_1$–C$_6$)alkyl-O—(C=O)—NH—, (C$_3$–C$_7$)cycloalkyl-O—(C=O)—NH—, (C$_6$–C$_{10}$)aryl-O—(C=O)—NH—, and (C$_1$–C$_9$)heteroaryl-O—(C=O)—NH—; preferably selected from the group consisting of (C$_1$–C$_6$)alkyl-O—(C=O)—NH— and (C$_6$–C$_{10}$)aryl-O—(C=O)—NH—; more preferably methyl-O—(C=O)—NH—.

In another embodiment of the invention, R$^4$ is a radical selected from the group consisting of (C$_1$–C$_6$)alkyl-NH—(C=O)—NH—, [(C$_1$–C$_6$)alkyl]$_2$—NH—(C=O)—NH—, (C$_3$–C$_7$)cycloalkyl-NH—(C=O)—NH—, (C$_6$–C$_{10}$)aryl-NH—(C=O)—NH—, and (C$_1$–C$_9$)heteroaryl]-NH—(C=O)—NH—; preferably selected from the group consisting of [(C$_1$–C$_6$)alkyl]-NH—(C=O)—NH—, [(C$_1$–C$_6$)alkyl]$_2$—NH—(C=O)—NH—, and [(C$_6$–C$_{10}$)aryl]-NH—(C=O)—NH—.

In another embodiment of the invention, R$^4$ is a radical selected from the group consisting of (C$_1$–C$_6$)alkyl-NH—HC=N—, [(C$_1$–C$_6$)alkyl]$_2$N—HC=N—, and (C$_6$–C$_{10}$)aryl-NH—HC=N—; preferably selected from the group consisting of [(C$_1$–C$_6$)alkyl]-NH—HC=N—, [C$_1$–C$_6$)alkyl]$_2$N—HC=N—, and [(C$_6$–C$_{10}$)aryl]-NH—HC=N—.

In another embodiment of the invention, R$^4$ is a radical selected from the group consisting of (C$_1$–C$_6$)alkyl-(C=O)—NH—, (C$_1$–C$_6$)alkyl-O—(C=O)—NH—, (C$_1$–C$_6$)alkyl-NH—, and [(C$_1$–C$_6$)alkyl]-NH—HC=N—; preferably selected from the group consisting of methyl-(C=O)—NH—, ethyl-(C=O)—NH—, sec-butyl-(C=O)—NH—, isobutyl-(C=O)—NH—, tert-butyl-(C=O)—NH—, methyl-O—(C=O)—NH—, ethyl-O—(C=O)—NH—, sec-butyl-O—(C=O)—NH—, isobutyl-O—(C=O)—NH—, tert-butyl-O—(C=O)—NH—, methyl-NH—, ethyl-NH—, sec-butyl-NH—, isobutyl-NH—, tert-butyl-NH—, methyl-NH—HC=N—, and ethyl-NH—HC=N—.

In another embodiment of the invention, B is —O—.

In another embodiment of the invention, B is —S—, —SO—, or —SO$_2$—.

In another embodiment of the invention, B is —SO$_2$—.

In another embodiment of the invention, B is R$^6$—N—; wherein R$^8$ is preferably H or methyl.

In another embodiment of the invention, R$^3$ is a radical selected from the group consisting of (C$_1$–C$_6$)alkyl; (C$_3$–C$_{10}$)cycloalkyl, and (C$_1$–C$_9$)heterocyclyl.

In another embodiment of the invention, R$^3$ is an (C$_1$–C$_6$) alkyl radical; preferably selected from the group consisting of methyl, ethyl, sec-butyl, isobutyl, and tert-butyl.

In another embodiment of the invention, R$^3$ is a (C$_3$–C$_{10}$) cycloalkyl radical; preferably selected from the group consisting of cyclopropyl, cyclobutyl, cyclopentyl, and cyclohexyl.

In another embodiment of the invention, R$^3$ is a (C$_1$–C$_9$) heterocyclyl radical; preferably selected from the group consisting of tetrahydrofuran-1-yl and tetrahydropyran-1-yl.

In another embodiment of any of the foregoing embodiments of the invention, the ring of the formula (R$^5$)-A-(SO$_m$R$^4$) is of the formula

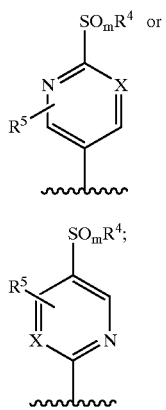

A1

A2 preferably A2; wherein X is >CR$^5$; wherein R$^5$ is preferably H, and m is 0, 1 or 2, preferably m is 2.

In another embodiment of any of the foregoing embodiments of the invention, the ring of the formula (R$^5$)-A-(SO$_m$R$^4$) is of the formula

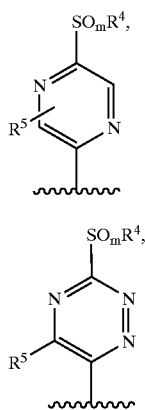

A3

A4

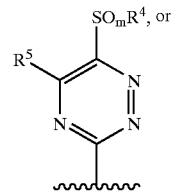

A5

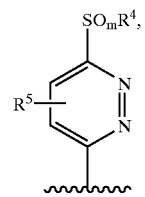

A6 wherein m is 0, 1 or 2, preferably m is 2.

In another embodiment of any of the foregoing embodiments of the invention, the ring of the formula (R$^5$)-A-(SO$_m$R$^4$) is of the formula

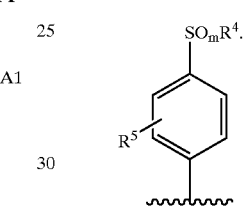

A7

In another embodiment of any of the foregoing embodiments of the invention, R$^1$ is a radical selected from the group consisting of —NO$_2$, —CN, (C$_1$–C$_6$)alkyl, (C$_1$–C$_6$) alkyl-SO$_2$—, (C$_1$–C$_6$)alkyl-(C═O)—, (C$_1$–C$_6$)alkyl-O—(C═O)—, and [(C$_1$–C$_6$)alkyl]$_2$—NH—(C═O).

In another embodiment of any of the foregoing embodiments of the invention, R$^1$ is a radical selected from the group consisting of H, —NO$_2$, and —CN; preferably R$^1$ is —CN.

In another embodiment of any of the foregoing embodiments of the invention, R$^1$ is a radical selected from the group consisting of H—(C═O)—, (C$_1$–C$_6$)alkyl-(C═O)—, (C$_1$–C$_6$)alkyl-O—(C═O)—, (C$_1$–C$_9$)heteroaryl-(C═O)—, and (C$_1$–C$_9$)heterocyclyl-(C═O)—.

In another embodiment of any of the foregoing embodiments of the invention, R$^1$ is a radical selected from the group consisting of H$_2$N—(C═O)—, (C$_1$–C$_6$)alkyl-NH—(C═O)—, [(C$_1$–C$_6$)alkyl]$_2$—N—(C═O)—, [(C$_6$–C$_{10}$) aryl]-NH—(C═O)—, [(C$_1$–C$_6$)alkyl]-[((C$_6$–C$_{10}$)aryl)-N]—(C═O)—, HO—NH—(C═O)—, and (C$_1$–C$_6$)alkyl-O—NH—(C═O)—.

In another preferred embodiment of any of the foregoing embodiments of the invention, R$^2$ is a radical selected from the group consisting of H, —NO$_2$, —CN, or (C$_1$–C$_6$)alkyl optionally substituted by one —OH substituent or by one to four fluoro substituents; preferably R$^2$ is an (C$_1$–C$_6$)alkyl radical optionally substituted by one —OH substituent or by one to four fluoro substituents; more preferably R$^2$ is —CF$_3$ or —CHF$_2$.

In another embodiment of any of the foregoing embodiments of the invention, R$^2$ is a radical selected from the group consisting of (C$_2$–C$_6$)alkenyl, (C$_2$–C$_6$)alkynyl, (C$_3$–C$_7$)cycloalkyl, (C$_6$–C$_{10}$)aryl, (C$_1$–C$_9$)heteroaryl, and (C$_1$–C$_9$)heterocyclyl.

In another embodiment of any of the foregoing embodiments of the invention, R$^2$ is a radical selected from the group consisting of $(C_1-C_6)$alkyl-O—, $(C_3-C_7)$cycloalkyl-O—, $(C_6-C_{10})$aryl-O—, $(C_1-C_9)$heteroaryl-O—, and $(C_1-C_9)$heterocyclyl-O—.

In another embodiment of any of the foregoing embodiments of the invention, $R^2$ is a radical selected from the group consisting of H—(C=O)—, $(C_1-C_6)$alkyl-(C=O)—, $(C_3-C_7)$cycloalkyl-(C=O)—, $(C_6-C_{10})$aryl-(C=O)—, $(C_1-C_9)$heteroaryl-(C=O)—, and $(C_1-C_9)$heterocyclyl-(C=O)—.

In another embodiment of any of the foregoing embodiments of the invention, $R^1$ is a radical selected from the group consisting of $(C_1-C_6)$alkyl-O—(C=O)—, $(C_3-C_7)$cycloalkyl-O—(C=O)—, $(C_6-C_{10})$aryl-O—(C=O)—, $(C_1-C_9)$heteroaryl-O—(C=O)— and $(C_1-C_9)$heterocyclyl-O—(C=O)—.

In another embodiment of any of the foregoing embodiments of the invention, $R^2$ is a radical selected from the group consisting of $(C_1-C_6)$alkyl-(C=O)—O—, $(C_3-C_7)$cycloalkyl-(C=O)—O—, $(C_6-C_{10})$aryl-(C=O)—O—, $(C_1-C_9)$heteroaryl-(C=O)—O—, and $(C_1-C_9)$heterocyclyl-(C=O)—O—.

In another embodiment of any of the foregoing embodiments of the invention, $R^2$ is a radical selected from the group consisting of $(C_1-C_6)$alkyl-(C=O)—NH—, $(C_3-C_7)$cycloalkyl-(C=O)—NH—, $(C_6-C_{10})$aryl-(C=O)—NH—, $(C_1-C_9)$heteroaryl-(C=O)—NH—, $(C_1-C_9)$heterocyclyl-(C=O)—NH—, and $(C_1-C_6)$alkyl-O—(C=O)—NH—.

In another embodiment of any of the foregoing embodiments of the invention, $R^2$ is a radical selected from the group consisting of $(C_1-C_6)$alkyl-NH—, $[(C_1-C_6)$alkyl$]_2$—N—, $(C_3-C_7)$cycloalkyl-NH—, $[(C_3-C_7)$cycloalkyl$]_2$—N—, $[(C_6-C_{10})$aryl]-NH—, $[(C_6-C_{10})$aryl$]_2$—N—, $[(C_1-C_6)$alkyl]-$[((C_6-C_{10})$aryl)-N]—, $[(C_1-C_9)$heteroaryl]-NH—, $[(C_1-C_9)$heteroaryl$]_2$—N—, $[(C_1-C_9)$heterocyclyl]-NH—, and $[(C_1-C_9)$heterocyclyl$]_2$—N—.

In another embodiment of any of the foregoing embodiments of the invention, $R^2$ is a radical selected from the group consisting of $H_2N$—(C=O)—, HO—NH—(C=O)—, and $(C_1-C_6)$alkyl-O—NH—(C=O)—.

In another embodiment of any of the foregoing embodiments of the invention, $R^2$ is a radical selected from the group consisting of $[(C_1-C_6)$alkyl]-NH—(C=O)—, $[(C_1-C_6)$alkyl$]_2$—N—(C=O)—, $[(C_3-C_7)$cycloalkyl]-NH—(C=O)—, $[(C_3-C_7)$cycloalkyl$]_2$—N—(C=O)—, $[(C_6-C_{10})$aryl]-NH—(C=O)—, $[(C_6-C_{10})$aryl$]_2$—N—(C=O)—, $[(C_1-C_6)$alkyl]-$[((C_6-C_{10})$aryl)-N]—(C=O)—, $[(C_1-C_9)$heteroaryl]-NH—(C=O)—, $[(C_1-C_9)$heteroaryl$]_2$—N—(C=O)—, $[(C_1-C_9)$heterocyclyl]-NH—(C=O)—, and $(C_1-C_6)$alkyl-S—.

In another embodiment of any of the foregoing embodiments of the invention, $R^5$ is H halo or —CN.

In another embodiment of any of the foregoing embodiments of the invention, $R^5$ is —OH or $(C_1-C_6)$alkyl-O—.

In another embodiment of any of the foregoing embodiments of the invention, $R^5$ is $(C_2-C_6)$alkenyl or $(C_2-C_6)$alkynyl.

In another embodiment of any of the foregoing embodiments of the invention, $R^5$ is $(C_3-C_7)$cycloalkyl.

In another embodiment of any of the foregoing embodiments of the invention, $R^5$ is H—(C=O)—, $(C_1-C_6)$alkyl-(C=O)—, $(C_1-C_6)$alkyl-(C=O)—O—, HO—(C=O)—, or $(C_1-C_6)$alkyl-O—(C=O)—.

In another embodiment of any of the foregoing embodiments of the invention, $R^5$ is $(C_1-C_6)$alkyl-NH—, $[(C_1-C_6)$alkyl$]_2$—N—, $(C_3-C_7)$cycloalkyl-NH—, $(C_6-C_{10})$aryl-NH—, $[(C_1-C_6)$alkyl]-$[((C_6-C_{10})$aryl)-N]—, or $(C_1-C_9)$heteroaryl-NH—.

In another embodiment of any of the foregoing embodiments of the invention, $R^5$ is $H_2N$—(C=O)—, $(C_1-C_6)$alkyl-NH—(C=O)—, $[(C_1-C_8)$alkyl$]_2$—N—(C=O)—, $(C_6-C_{10})$aryl-(C=O)—, $[(C_1-C_6)$alkyl]-$[((C_6-C_{10})$aryl)-N]—(C=O)—, or $(C_1-C_6)$alkyl-O—NH—(C=O)—.

In another embodiment of any of the foregoing embodiments of the invention, $R^5$ is $(C_1-C_6)$alkyl-S—.

In a preferred embodiment of the present invention, $R^5$ is H.

In another embodiment of the invention, $R^6$ is H.

In another embodiment of the invention, $R^6$ is $(C_1-C_6)$alkyl, preferably methyl.

In another embodiment of the invention, $R^6$ is a radical selected from the group consisting of $(C_6-C_{10})$aryl, $(C_3-C_{10})$cycloalkyl, $(C_1-C_9)$heteroaryl and $(C_1-C_9)$heterocyclyl.

In a preferred embodiment of the invention, $R^4$ is a radical selected from the group consisting of methyl-NH—, ethyl-NH, cyclopropyl-$CH_2$—NH—, cyclopentyl-NH—, cyclohexyl-NH—, methyl-NH—HC=N—, and [methyl]$_2$N—HC=N—; B is —O—, —N— or —$SO_2$—; $R^3$ is a radical selected from the group consisting of sec-butyl, isobutyl, tert-butyl, —$CH_2$— (cyclobutyl), and —$CH_2$—(tetrahydrofuran-2-yl); the ring of the formula $(R^5)$-A-$(SO_mR^4)$ is of the formula

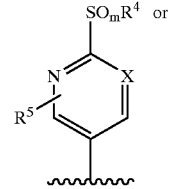

A1

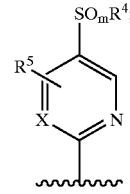

A2 more preferably A2; wherein X is >CH and m is 2; $R^1$ is —CN; $R^2$ is a radical selected from the group consisting of —$CF_3$ and —$CHF_2$; and $R^5$ is H.

Specific preferred compounds of formula I are selected from the group consisting of:

6-[4-Cyano-5-(2,2-dimethyl-propylamino)-3-trifluoromethyl-pyrazol-1-yl]-pyridine-3-sulfonic acid acetyl-amide;

6-[4-Cyano-5-(2,2-dimethyl-propylamino)-3-trifluoromethyl-pyrazol-1-yl]-pyridine-3-sulfonic acid propionyl-amide;

6-[4-Cyano-5-(2,2-dimethyl-propylamino)-3-trifluoromethyl-pyrazol-1-yl]-pyridine-3-sulfonic acid isobutyryl-amide;

6-[4-Cyano-5-(2,2-dimethyl-propylamino)-3-trifluoromethyl-pyrazol-1-yl]-pyridine-3-sulfonic acid (2,2-dimethyl-propionyl)-amide;

6-[4-Cyano-5-(2,2-dimethyl-propylamino)-3-trifluoromethyl-pyrazol-1-yl]-pyridine-3-sulfonic acid (1,1-dimethyl)-ethoxy-amide;

6-[4-Cyano-5-(2,2-dimethyl-propylamino)-3-trifluoromethyl-pyrazol-1-yl]-pyridine-3-sulfonic acid (3-methyl-butyryl)-amide;

6-(4-Cyano-5-cyclopentylmethoxy-3-trifluoromethyl-pyrazol-1-yl)-pyridine-3-sulfonic acid acetyl amide;

6-(4-Cyano-5-cyclopentylmethoxy-3-trifluoromethyl-pyrazol-1-yl)-pyridine-3-sulfonic acid propionyl amide;

6-(4-Cyano-5-cyclopentylmethoxy-3-trifluoromethyl-pyrazol-1-yl)-pyridine-3-sulfonic acid isobutyryl amide;

6-[4-Cyano-5-(2,2-dimethyl-propoxy)-3-trifluoromethyl-pyrazol-1-yl]-pyridine-3-sulfonic acid (1,1-dimethylethoxy) amide;

6-[4-Cyano-5-(2,2-dimethyl-propoxy)-3-trifluoromethyl-pyrazol-1-yl]-pyridine-3-sulfonic acid (3-methyl-butyryl) amide;

6-[4-Cyano-5-(2,2-dimethyl-propoxy)-3-trifluoromethyl-pyrazol-1-yl]-pyridine-3-sulfonic acid acetyl amide;

6-[4-Cyano-5-(3-methyl-cyclohexyloxy)-3-trifluoromethyl-pyrazol-1-yl]-pyridine-3-sulfonic acid propionyl amide;

6-[4-Cyano-5-(3-methyl-cyclohexyloxy)-3-trifluoromethyl-pyrazol-1-yl]-pyridine-3-sulfonic acid isobutyryl amide;

6-[4-Cyano-5-(3-methyl-cyclohexyloxy)-3-trifluoromethyl-pyrazol-1-yl]-pyridine-3-sulfonic acid (1,1-dimethylethoxy) amide;

6-(5-sec-Butylsulfanyl-4-cyano-3-trifluoromethyl-pyrazol-1-yl)-pyridine-3-sulfonic acid acetyl amide;

6-(5-sec-Butylsulfanyl-4-cyano-3-trifluoromethyl-pyrazol-1-yl)-pyridine-3-sulfonic acid (3-methyl-butyryl) amide;

6-(5-sec-Butylsulfanyl-4-cyano-3-trifluoromethyl-pyrazol-1-yl)-pyridine-3-sulfonic acid (1,1-dimethylethoxy) amide;

6-(5-sec-Butylsulfanyl-4-cyano-3-difluoromethyl-pyrazol-1-yl)-pyridine-3-sulfonic acid acetyl amide;

6-(5-sec-Butylsulfanyl-4-cyano-3-difluoromethyl-pyrazol-1-yl)-pyridine-3-sulfonic acid propionyl amide; and 6-(5-sec-Butylsulfanyl-4-cyano-3-difluoromethyl-pyrazol-1-yl)-pyridine-3-sulfonic acid isobutyryl amide; or the pharmaceutically acceptable salts thereof.

The present invention also relates to a pharmaceutical composition for the treatment of a condition selected from the group consisting of arthritis (including osteoarthritis, degenerative joint disease, spondyloarthropathies, gouty arthritis, systemic lupus erythematosus, juvenile arthritis and rheumatoid arthritis), fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in cats), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock) and septic shock (preferably arthritis, fever, common cold, pain and cancer) in a mammal, preferably a human, cat, livestock or a dog, comprising an amount of a compound of formula I or a pharmaceutically acceptable salt thereof effective in such treatment and a pharmaceutically acceptable carrier.

The present invention also relates to a pharmaceutical composition for the treatment of a condition that can be treated by selectively inhibiting COX-2 in a mammal, preferably a human, cat, livestock or dog, comprising a COX-2 selective inhibiting effective amount of a compound of formula I or a pharmaceutically acceptable salt thereof and a pharmaceutically acceptable carrier.

The present invention also relates to a pharmaceutical composition for the treatment of a condition selected from the group consisting of inflammatory diseases such as arthritis (including osteoarthritis, degenerative joint disease, spondyloarthropathies, gouty arthritis, systemic lupus erythematosus, juvenile arthritis and rheumatoid arthritis), or fever (including rheumatic fever and fever associated with influenza).

The present invention also relates to a method for treating a condition selected from the group consisting of arthritis (including osteoarthritis, degenerative joint disease, spondyloarthropathies, gouty arthritis, systemic lupus erythematosus, juvenile arthritis and rheumatoid arthritis), fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in cats), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock) and septic shock (preferably arthritis, fever, common cold, pain and cancer) in a mammal, preferably a human, cat, livestock or a dog, comprising administering to said mammal an amount of a compound of formula I or a pharmaceutically acceptable salt thereof effective in treating such a condition.

The present invention also relates to a method for treating a disorder or condition that can be treated by selectively inhibiting COX-2 in a mammal, preferably a human, cat, livestock or a dog, comprising administering to a mammal requiring such treatment a COX-2 selective inhibiting effective amount of a compound of formula I or a pharmaceutically acceptable salt thereof.

The present invention also relates to a method for treating a condition selected from the group consisting of inflammatory diseases such as arthritis (including osteoarthritis, degenerative joint disease, spondyloarthropathies, gouty arthritis, systemic lupus erythematosus, juvenile arthritis and rheumatoid arthritis), or fever (including rheumatic fever and fever associated with influenza).

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "livestock animals" as used herein refers to domesticated quadrupeds, which includes those being raised for meat and various byproducts, e.g., a bovine animal including cattle and other members of the genus *Bos*, a porcine animal including domestic swine and other members of the genus *Sus*, an ovine animal including sheep and other members of the genus *Ovis*, domestic goats and other members of the genus *Capra*; domesticated quadrupeds being raised for specialized tasks such as use as a beast of burden, e.g., an equine animal including domestic horses and other members of the family Equidae, genus *Equus*, or for searching and sentinel duty, e.g., a canine animal including domestic dogs and other members of the genus *Canis*; and domesticated quadrupeds being raised primarily for recreational purposes, e.g., members of *Equus* and *Canis*, as well as a feline animal including domestic cats and other members of the family Felidae, genus *Felis*.

The term "selective" as used herein, refers to COX-1/COX-2 $IC_{50}$ inhibition ratio of 5 or greater as determined for one of the in vitro, in vivo, or ex vivo assays described on pages 36–41.

The term "Companion animals" as used herein refers to cats, dogs and horses. As used herein, the term "dog(s)" denotes any member of the species *Canis familiaris*, of which there are a large number of different breeds. While laboratory determinations of biological activity may have been carried out using a particular breed, it is contemplated that the inhibitory compounds of the present invention will be found to be useful for treating pain and inflammation in any of these numerous breeds. Dogs represent a particularly preferred class of patients in that they are well known as being very susceptible to chronic inflammatory processes such as osteoarthritis and degenerative joint disease, which in dogs often results from a variety of developmental diseases, e.g., hip dysplasia and osteochondrosis, as well as from traumatic injuries to joints. Conventional NSAIDs, if used in canine therapy, have the potential for serious adverse gastrointestinal reactions and other adverse reactions including kidney and liver toxicity. Gastrointestinal effects such as single or multiple ulcerations, including perforation and hemorrhage of the esophagus, stomach, duodenum or small and large intestine, are usually debilitating, but can often be severe or even fatal.

The term "treating reproductive disorders (preferably in livestock)" as used herein refers to the use of the COX-2 inhibitors of the invention in mammals, preferably livestock animals (cattle, pigs, sheep, goats or horses), during the estrus cycle to control the time of onset of estrus by blocking the uterine signal for lysis of the corpus luteum, i.e. F-series prostaglandins, then removing the inhibition when the onset of estrus is desired. There are settings where it is useful to control or synchronize the time of estrus, especially when artificial insemination or embryo transfer are to be performed. Such use also includes enhancing the rate of embryo survival in pregnant livestock animals. Blocking F-series prostaglandin release can have several beneficial actions including reducing uterine contractions, enhancing uteroplacental bloodflow, supporting recognition of pregnancy and postponing lysis of the corpus luteum at the time when estrus would have occurred had the animal not become pregnant (around Day 21 of pregnancy). Such treatment also abrogates the effects of stress on reproduction. For example reductions in fertility caused by excessive heat, negative energy balance and other stresses which have a COX-2 mediated component, as does abortion induced by stress such as heat, transportation, co-mingling, palpation, infection, etc. Such treatment is also useful to control the time of parturition, which is accompanied by release of F-series prostaglandins that lead to lysis of the corpus luteum. Inhibition of COX-2 would block the onset of premature labor in livestock animals, allowing the offspring time to mature before birth. Also there are settings where controlling the time of parturition is a useful tool for management of pregnant animals.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, prodrugs thereof and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing prodrugs of compounds of the formula I. This invention also encompasses methods of treating disorders that can be treated by the selective inhibition of COX-2 comprising administering prodrugs of compounds of the formula I. Compounds of formula I having free amino, amido, hydroxy, carboxylic acid ester, sulfonamide or carboxylic groups (especially alkyl-S— and alkyl-(S=O)—) can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters are covalently bonded to the above substituents of formula I through the carbonyl carbon prodrug sidechain. Prodrugs also include metabolically labile groups such as ethers, acetates, mercaptans and sulfoxides.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies and TNF receptor immunoglobulin molecules (such as Enbrel®), low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

This invention also relates to a method of or a pharmaceutical composition for treating inflammatory processes and diseases comprising administering a compound of formula I of this invention or its salt to a mammal including a human, cat, livestock or dog, wherein said inflammatory processes and diseases are defined as above and said inhibitory compound is used in combination with one or more other therapeutically active agents under the following conditions:

A.) where a joint has become seriously inflamed as well as infected at the same time by bacteria, fungi, protozoa and/or virus, said inhibitory compound is administered in combination with one or more antibiotic, antifungal, antiprotozoal and/or antiviral therapeutic agents;

B.) where a multi-fold treatment of pain and inflammation is desired, said inhibitory compound is administered in combination with inhibitors of other mediators of inflammation, comprising one or more members independently selected from the group consisting essentially of:
 (1) NSAIDs;
 (2) $H_1$-receptor antagonists;
 (3) kinin-$B_1$- and $B_2$-receptor antagonists;
 (4) prostaglandin inhibitors selected from the group consisting of PGD-, PGF-$PGI_2$- and PGE-receptor antagonists;
 (5) thromboxane $A_2$ ($TXA_2$—) inhibitors;
 (6) 5-, 12- and 15-lipoxygenase inhibitors;
 (7) leukotriene $LTC_4$—, $LTD_4/LTE_4$- and $LTB_4$- inhibitors;
 (8) PAF-receptor antagonists;
 (9) gold in the form of an aurothio group together with one or more hydrophilic groups;
 (10) immunosuppressive agents selected from the group consisting of cyclosporine, azathioprine and methotrexate;
 (11) anti-inflammatory glucocorticoids;
 (12) penicillamine;
 (13) hydroxychloroquine;
 (14) anti-gout agents including colchicine; xanthine oxidase inhibitors including allopurinol; and uricosuric agents selected from probenecid, sulfinpyrazone and benzbromarone;

C. where older mammals are being treated for disease conditions, syndromes and symptoms found in geriatric mammals, said inhibitory compound is administered in combination with one or more members independently selected from the group consisting essentially of:
 (1) cognitive therapeutics to counteract memory loss and impairment;
 (2) anti-hypertensives and other cardiovascular drugs intended to offset the consequences of atherosclerosis, hypertension, myocardial ischemia, angina, congestive heart failure and myocardial infarction, selected from the group consisting of:
  a. diuretics;
  b. vasodilators;
  c. β-adrenergic receptor antagonists;
  d. angiotensin-II converting enzyme inhibitors (ACE-inhibitors), alone or optionally together with neutral endopeptidase inhibitors;
  e. angiotensin II receptor antagonists;
  f. renin inhibitors;
  g. calcium channel blockers;
  h. sympatholytic agents;
  i. $α_2$-adrenergic agonists;
  j. α-adrenergic receptor antagonists; and
  k. HMG-CoA-reductase inhibitors (anti-hypercholesterolemics);
 (3) antineoplastic agents selected from:
  a. antimitotic drugs selected from:
   i. vinca alkaloids selected from:

[1] vinblastine and
[2] vincristine;
(4) growth hormone secretagogues;
(5) strong analgesics;
(6) local and systemic anesthetics; and
(7) $H_2$-receptor antagonists, proton pump inhibitors and other gastroprotective agents.

The active ingredient of the present invention may be administered in combination with inhibitors of other mediators of inflammation, comprising one or more members selected from the group consisting essentially of the classes of such inhibitors and examples thereof which include, matrix metalloproteinase inhibitors, aggrecanase inhibitors, TACE inhibitors, leucotriene receptor antagonists, IL-1 processing and release inhibitors, ILra, $H_1$-receptor antagonists; kinin-$B_1$- and $B_2$-receptor antagonists; prostaglandin inhibitors such as PGD-, PGF-$PGI_2$- and PGE-receptor antagonists; thromboxane $A_2$ (TXA2-) inhibitors; 5- and 12-lipoxygenase inhibitors; leukotriene $LTC_4$-, $LTD_4/LTE_4$- and $LTB_4$-inhibitors; PAF-receptor antagonists; gold in the form of an aurothio group together with various hydrophilic groups; immunosuppressive agents, e.g., cyclosporine, azathioprine and methotrexate; anti-inflammatory glucocorticoids; penicillamine; hydroxychloroquine; anti-gout agents, e.g., colchicine, xanthine oxidase inhibitors, e.g., allopurinol and uricosuric agents, e.g., probenecid, sulfinpyrazone and benzbromarone.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine and antimetabolites such as methotrexate.

The compounds of the present invention may also be used in combination with anti-hypertensives and other cardiovascular drugs intended to offset the consequences of atherosclerosis, including hypertension, myocardial ischemia including angina, congestive heart failure and myocardial infarction, selected from vasodilators such as hydralazine, β-adrenergic receptor antagonists such as propranolol, calcium channel blockers such as nifedipine, $α_2$-adrenergic agonists such as clonidine, α-adrenergic receptor antagonists such as prazosin and HMG-CoA-reductase inhibitors (anti-hypercholesterolemics) such as lovastatin or atorvastatin.

The active ingredient of the present invention may also be administered in combination with one or more antibiotic, antifungal, antiprotozoal, antiviral or similar therapeutic agents.

The compounds of the present invention may also be used in combination with CNS agents such as antidepressants (such as sertraline), anti-Parkinsonian drugs (such as L-dopa, requip, mirapex, MAOB inhibitors such as selegine and rasagiline, comP inhibitors such as Tasmar, A-2 inhibitors, dopamine reuptake inhibitors, NMDA antagonists, nicotine agonists, dopamine agonists and inhibitors of neuronal nitric oxide synthase) and anti-Alzheimer's drugs such as donepezil, tacrine, COX-2 inhibitors, propentofylline or metryfonate.

The compounds of the present invention may also be used in combination with osteoporosis agents such as roloxifene, lasofoxifene, droloxifene or fosomax and immunosuppressant agents such as FK-506 and rapamycin.

The present invention also relates to the formulation of the active agents of the present invention alone or with one or more other therapeutic agents which are to form the intended combination, including wherein said different drugs have varying half-lives, by creating controlled-release forms of said drugs with different release times which achieves relatively uniform dosing; or, in the case of non-human patients, a medicated feed dosage form in which said drugs used in the combination are present together in admixture in said feed composition. There is further provided in accordance with the present invention co-administration in which the combination of drugs is achieved by the simultaneous administration of said drugs to be given in combination; including co-administration by means of different dosage forms and routes of administration; the use of combinations in accordance with different but regular and continuous dosing schedules whereby desired plasma levels of said drugs involved are maintained in the patient being treated, even though the individual drugs making up said combination are not being administered to said patient simultaneously.

DETAILED DESCRIPTION OF THE INVENTION

The following reaction Schemes illustrate the preparation of the compounds of the present invention. Unless otherwise indicated, the ring of the formula $(R^5)$-A-$(SO_mR^4)$, m, X, and $R^1$ through $R^6$ in the reaction schemes and discussion that follow are as defined above.

Scheme 1

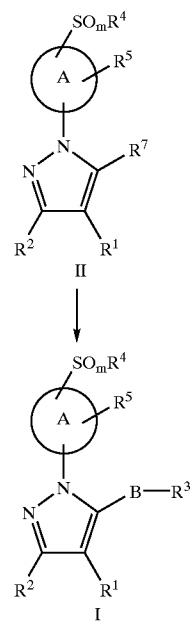

Scheme 2

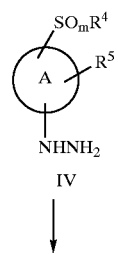

-continued
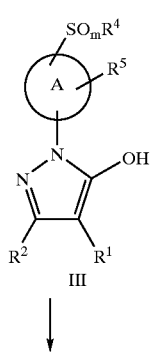
III
↓
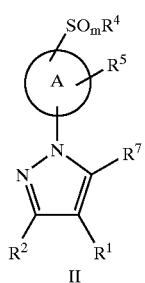
II
Scheme 3
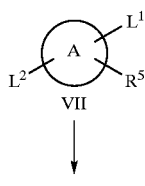
VII
↓
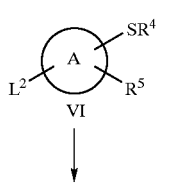
VI
↓
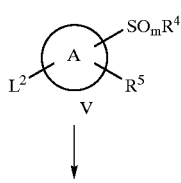
V
↓
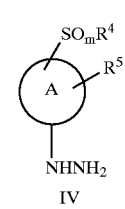
IV
Scheme 1 refers to the preparation of a compound of formula I.
Referring to Scheme 1, a compound of formula I (i.e., a compound of the formulae IA1–IA7, respectively):
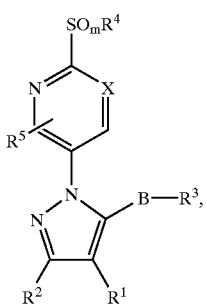
IA1
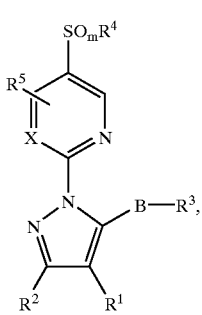
IA2
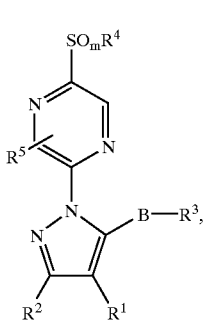
IA3
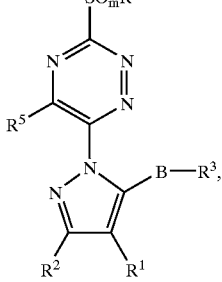
IA4

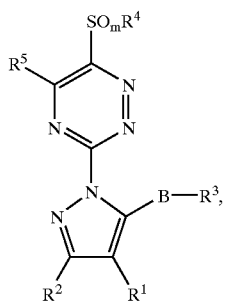
IA5
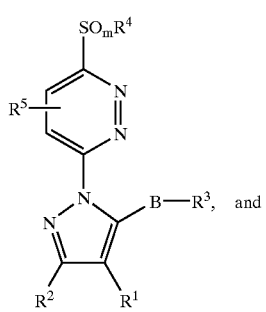
IA6
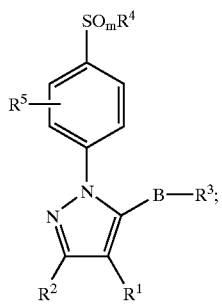
IA7
can be prepared by reacting a compound of formula II, i.e., a compound of formulae IIA1–IIA7, respectively:
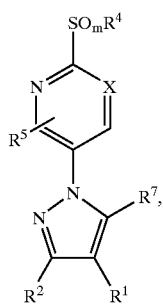
IIA1
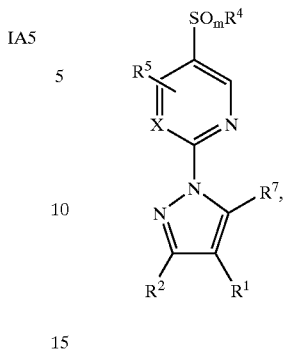
IIA2
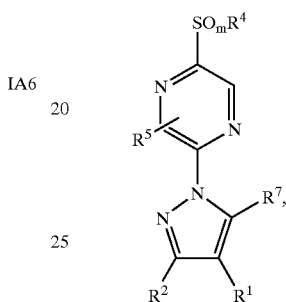
IIA3
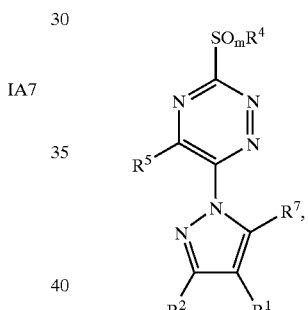
IIA4
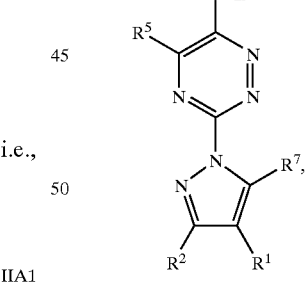
IIA5
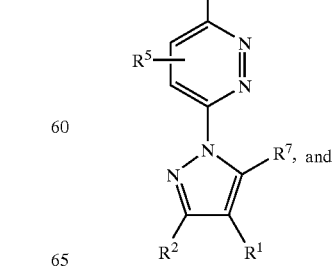
IIA6

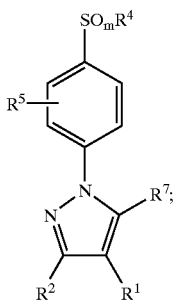

IIA7 wherein R⁷ is a leaving group, with a compound of the formula R³—B—H in the presence of a fluoride containing salt and in the presence of a solvent.

The above compounds of the formula R³—B—H are commercially available or can be prepared by the methods described in Jerry March, "Advanced Organic Chemistry", 4th edition, 1992, and references cited therein.

Suitable leaving groups R⁷ of the compound of formula II include halo, such as fluoro, chloro, iodo, or bromo. Other suitable leaving groups include $(C_1-C_6)$alkyl-$SO_3$—, such as $CH_3$—$SO_3$—, $CF_3$—$SO_3$—, or $CF_3CF_2$—$SO_3$—. Other suitable leaving groups include $(C_6-C_{10})$aryl-$SO_3$—, such as tosyl-$SO_3$— or phenyl-$SO_3$—. Other suitable leaving groups include $(C_1-C_6)$alkyl-$SO_2$—, such as $CH_3$—$SO_2$—; or $(C_6-C_{10})$aryl-$SO_2$—, such as phenyl-$SO_2$—. Preferably, the leaving group R⁷ is halo, such as chloro; or $(C_1-C_6)$ alkyl-$SO_3$—, such as $CF_3$—$SO_3$—, or $CF_3CF_2$—$SO_3$—.

Suitable fluoride containing salts include a metal salt, such as lithium, sodium, potassium, cesium, magnesium, calcium, strontium and barium. Other suitable fluoride salts include tetra$(C_1-C_8)$alkylammonium fluoride, such as tetrabutylammonium fluoride; or $(C_1-C_{16})$alkyltri$(C_1-C_2)$ alkylammonium fluoride, such as cetyltrimethylammonium fluoride.

The aforesaid reaction can be performed in the presence of about 0.05 to about 10 equivalents; more preferably about 0.05 to about 5 equivalents; most preferably about 0.1 to about 2 equivalents; of the fluoride containing salts relative to the compound of formula I.

Unless otherwise indicated, the term "equivalents" refers to the number of moles of the fluoride containing salt relative to the number of moles of the compound of the formula I.

Suitable solvents used in the aforesaid reaction include acetonitrile, dichloromethane, chloroform, tetrahydrofuran, dichloroethane, dimethylsulfoxide, dimethylformamide, dimethylacetamide, or acetone.

The aforesaid reaction can be performed at a temperature of about 10° C. to about 100° C., preferably about 20° C. to about 80° C. The aforesaid reaction can be performed for a period from about 2 hours to about 96 hours, preferably from about 12 hours to about 48 hours.

In the aforesaid reaction, when the fluoride containing salt is a metal salt such as potassium fluoride or cesium fluoride; preferred solvents include dimethylsulfoxide, dimethylformamide, dimethylacetamide, acetone, or acetonitrile. Preferably, the aforesaid reaction is performed at a temperature of about 10° C. to about 30° C. Preferably, the aforesaid reaction is performed in the presence of about 0.05 to about 5 equivalents of the fluoride containing salts relative to the compound of formula I.

In the aforesaid reaction, when the fluoride containing salt is tetra$(C_1-C_8)$alkylammonium fluoride or $(C_1-C_{16})$alkyltri $(C_1-C_2)$alkylammonium fluoride; preferred solvents include acetonitrile, dichloromethane, chloroform, tetrahydrofuran, or dichloroethane. Preferably, the aforesaid reaction is performed at a temperature of about 20° C. to about 80° C. Preferably, the aforesaid reaction is performed in the presence of about 0.1 to about 2 equivalents of the fluoride containing salts relative to the compound of formula I.

Scheme 2 illustrates methods of preparing compounds of the formula II, which are intermediates useful in preparing compounds of the formula I in Scheme 1.

Referring to Scheme 2, a compound of the formula II wherein R⁷ is halo can be prepared by reacting a compound of the formula III with a halogenating agent in a polar solvent. Suitable halogenating agents include oxalyl chloride, $POCl_3$, $POBr_3$, $SOCl_2$ or $PCl_5$, preferably $POCl_3$. Suitable solvents include methylene chloride, N,N-dimethylformamide (DMF), N,N-dimethylacetamide (DMA) or N-methyl-2-pyrrolidinone (NMP), preferably methylene chloride. The aforesaid reaction is generally carried out at a temperature from about 20° C. to about 140° C., preferably at about the reflux temperature of the polar solvent, preferably when the solvent is methylene chloride, the temperature is 55° C. The aforesaid reaction is generally carried out for a period from about 1 hour to about 48 hours, preferably about 2 hours to about 24 hours.

A compound of the formula II wherein R⁷ contains a —$SO_3$—, such as $(C_1-C_6)$alkyl-$SO_3$— or $(C_6-C_{10})$aryl-$SO_3$—, can be prepared by reacting a compound of the formula III with a sulfonylating agent in a polar solvent. Suitable sulfonylating agents include trifluoromethanesulfonic anhydride, methanesulfonyl chloride, or methanesulfonyl anhydride, preferably methanesulfonyl chloride. Suitable solvents for the aforesaid reaction include methylene chloride, N,N-dimethylformamide (DMF), N,N-dimethylacetamide (DMA) or N-methyl-2-pyrrolidinone (NMP), preferably methylene chloride. The aforesaid reaction is generally carried out at a temperature from about -10° C. to about 25° C., preferably at about 0° C. The aforesaid reaction is generally carried out for a period from about 1 hour to about 48 hours.

A compound of the formula II wherein said R⁷ contains a —$SO_2$—, such as $(C_1-C_6)$alkyl-$SO_2$— or $(C_6-C_{10})$aryl-$SO_2$—, can be prepared by reacting a compound of the formula II wherein R⁷ is halo or contains a —$SO_3$—, as defined above, with a sulfonating agent in a polar solvent. Suitable sulfonating agents include $NaSO_3CH_3$ or $NaSO_3$ $(C_6-C_{10})$aryl. Other suitable sulfonating agents include NaS $(C_1-C_6)$alkyl, such as $NaSCH_3$, or NaS$(C_6-C_{10})$aryl, such as NaS$(C_6H_5)$, followed by an oxidizing agent, such as OXONE®, metachloroperbenzoic acid, or hydrogen peroxide. Suitable solvents for the aforesaid reaction include DMF, DMA, or DMSO, preferably DMSO. The aforesaid reaction is generally carried out at a temperature from about minus 10° C. to about 120° C., preferably at about 100° C. The aforesaid reaction is generally carried out for a period from about 1 hour to about 48 hours, preferably about 4 hours to about 24 hours.

Compounds of the formula III can be prepared by reacting a compound of formula IV, wherein the ring of the formula $(R^5)\text{-A-}(SO_mR^4)$ is as defined above, with a reagent of the formula

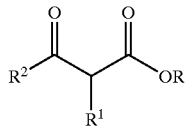

wherein R is $(C_1-C_6)$alkyl, such as methyl; in a suitable solvent under acidic, neutral or basic conditions. Preferably, the reagent is 4,4,4-trifluoro-3-oxo-butyric acid methyl ester. Suitable solvents include methanol, ethanol, DMF, DMSO, water or a mixture thereof. Suitable acids include hydrochloric acid or trifluoroacetic acid. Suitable bases include sodium hydroxide, potassium hydroxide and potassium carbonate. The aforesaid reaction is generally carried out at a temperature from about 0° C. to about 140° C., preferably at about 20° C. to about 100° C., most preferably at about 20° C. to about 100° C. The aforesaid reaction is generally carried out for a period from about 1 hour to about 24 hours, preferably from about 6 hours to about 16 hours.

The above reagents of formula $R^2\text{—}(C\text{=}O)\text{—}CH(R^1)\text{—}(C\text{=}O)\text{—}OR$ are commercially available or can be prepared according to the methods described in Jerry March, "Advanced Organic Chemistry", 4th edition, 1992, and references cited therein.

Compounds of formula IV are commercially available or can be made by methods well known to those of ordinary skill in the art or according to Scheme 3. For example, compounds of formula IV can be prepared by the method described in Vavrina, et al,. *Collection Czechoslov. Chem. Commun.*, Vol. 37, 1721 (1972), which is incorporated herein by reference.

Scheme 3 refers to a preparation of a compound of the formula IV, which are intermediates useful in preparing compounds of the formula II in Scheme 2.

Referring to Scheme 3, a compound of the formula IV (i.e., a compound of the formulae IVA1–IVA7, respectively):

IVA1
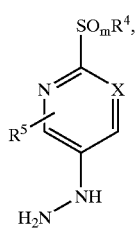

IVA2
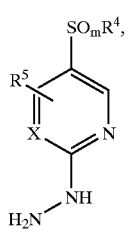

IVA3
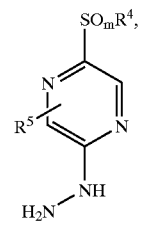

IVA4
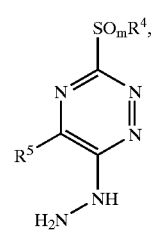

IVA5
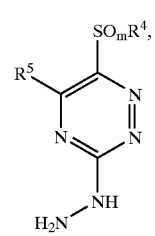

IVA6
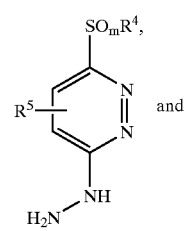

and

IVA7
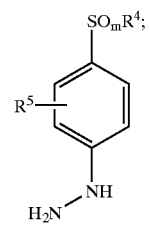

wherein m is 1, or 2, can be prepared by reacting a compound of the formula V (i.e., a compound of the formulae VA1–VA7, respectively):

VA1
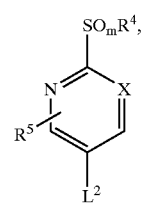

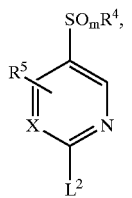

VA2

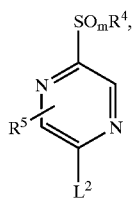

VA3

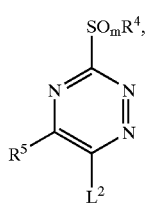

VA4

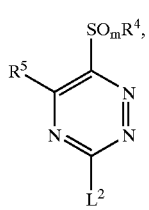

VA5

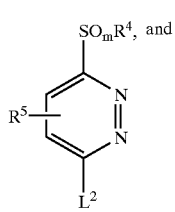

VA6

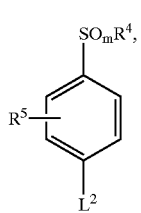

VA7 wherein $L^2$ is a leaving group and m is 1 or 2, with hydrazine (preferably anhydrous hydrazine) in the presence of a polar solvent. Suitable leaving groups $L_2$ include halo, triflate, or methylsulfonyl, preferably halo, such as chloro and bromo. Suitable solvents include alcohol (such as ethanol, methanol, propanol or butanol), DMSO, DMF, DMA, or NMP, preferably alcohol, most preferably ethanol. This reaction can be carried out at a temperature from about 0° C. to about 140° C., preferably at about the reflux temperature of the solvent. This reaction can be carried out for a period of from about 1 hour to about 36 hours, preferably from about 2 hours to about 24 hours. Preferably the product is isolated as a salt, such as a hydrobromide or hydrochloride salt. The hydrochloride salt is preferred.

The compound of the formula IV wherein m is 0 can be prepared by reacting a compound of the formula VI (i.e., a compound of the formulae VIA1–VIA7, respectively):

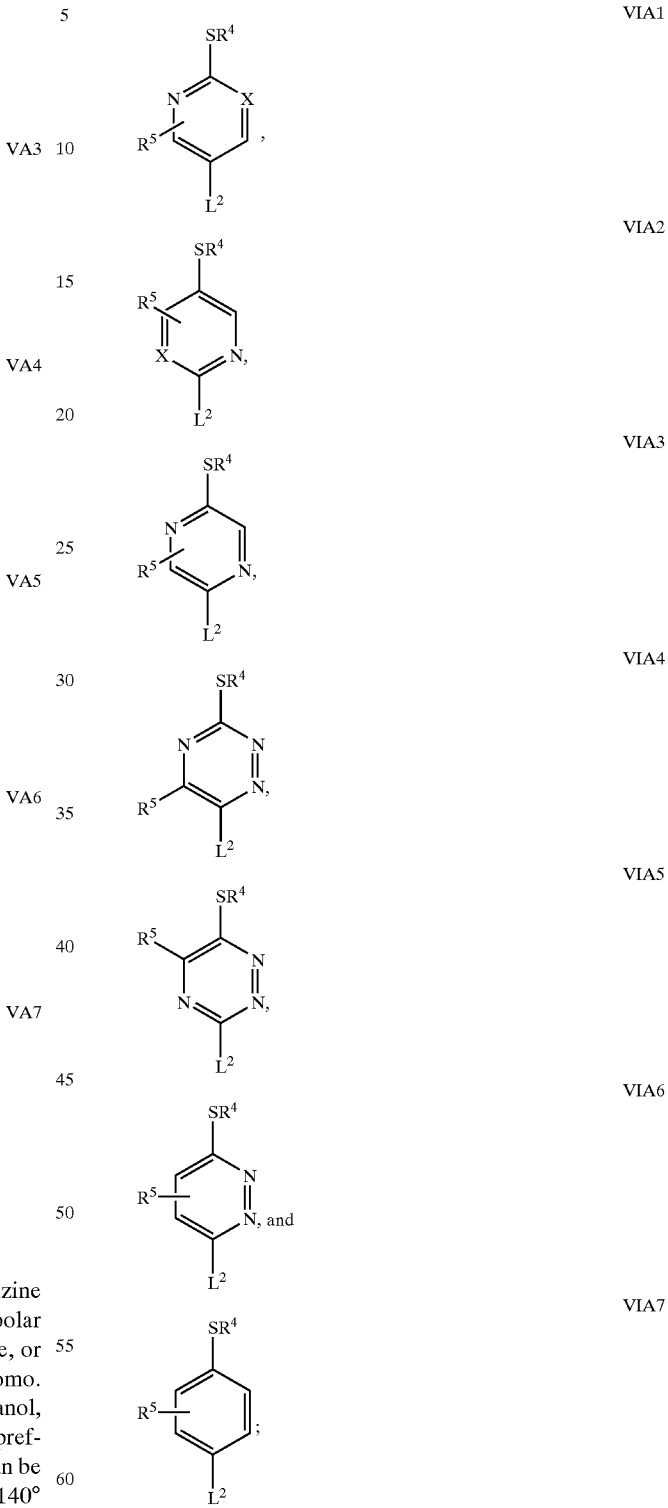

wherein $L^2$ is a leaving group, with hydrazine (preferably anhydrous hydrazine) in the presence of a polar solvent, under the condition described in the aforesaid paragraph.

The compound of the formula V (i.e., a compound of the formulae VA1–VA7, respectively, as defined above) can be prepared by reacting a compound of the formula VI (i.e., a compound of the formulae VIA1–VIA7, respectively, as defined above), wherein $L_2$ is a leaving group, with an oxidizing reagent in the presence of a solvent. Suitable oxidizing agents include meta-chloroperbenzoic acid, hydrogen peroxide, sodium perborate, or OXONE®, preferably OXONE®. Suitable solvents or solvent mixtures include methanol-water, dioxane-water, tetrahydrofuran-water, methylene chloride, or chloroform, preferably methanol-water or methylene chloride. The aforesaid reaction can be carried out at a temperature from about 0° C. to about 60° C., preferably the temperature may range from about 20° C. to about 25° C. (i.e. room temperature). The aforesaid reaction can be carried out for a period of from about 0.5 hours to about 24 hours, preferably about 16 hours.

The compounds of the formula VI (i.e., a compound of the formulae VIA1–VIA7, respectively, as defined above) can be prepared from a compound of formula VII (i.e., a compound of the formulae VIIA1–VIIA7, respectively):

VIIA1
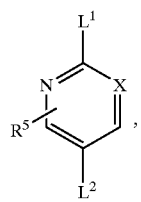

VIIA2
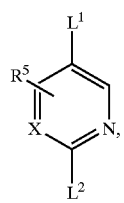

VIIA3
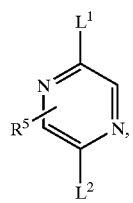

VIIA4
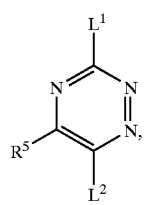

VIIA5
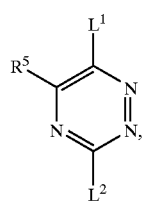

VIIA6
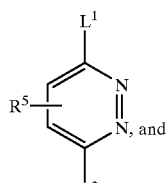
, and

VIIA7
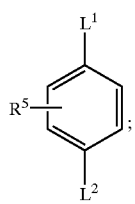
;

wherein each of $L^1$ and $L^2$ independently is a leaving group, by reacting said compound of the formula VII with a sulfur reagent in the presence or absence of a base in a polar solvent. Suitable leaving groups $L^1$ include halo or methyl-$SO_2$—, preferably halo, such as bromo or iodo. Suitable leaving groups $L^2$ halo or methyl-$SO_2$—, preferably halo, such as bromo or iodo. Suitable sulfur reagents include $(C_1-C_6)$alkyl-SH, $(C_1-C_6)$alkyl-S—S—$(C_1-C_6)$alkyl, $(C_1-C_6)$alkyl-$SO_3$—, NaS-$(C_1-C_6)$alkyl or KS-$(C_1-C_6)$alkyl. Suitable bases include sodium hydroxide, triethylamine, alkyllithiums (such as n-butyllithium, sec-butyllithium and tert-butyllithium) and lithium diisopropylamide. Suitable solvents include dialkylethers (such as dimethylether), alcohol (such as methanol, ethanol and tert-butanol), THF, benzene, toluene, xylene, DMF, DMSO, dioxane, 1,2-dimethoxyethane and a mixture of an alcohol and water. The aforesaid reaction can be carried out at a temperature from about −78° C. to 200° C., preferably the temperature may range from about −78° C. to about 120° C. The aforesaid reaction can be carried out for a period of from about 1 minute to about 24 hours.

Compounds of the formula VII (i.e., a compound of the formulae VIIA1–VIIA7, respectively, as defined above) may be prepared by methods well known to those of ordinary skill in the art (see for example, EP 1104760).

Unless indicated otherwise, the pressure of each of the above reactions is not critical. Generally, the reactions will be conducted at a pressure of about one to about three atmospheres, preferably at ambient pressure (about one atmosphere).

Those skilled in the art will appreciate that the above schemes describe general methods for preparing the compounds of the invention. Specific compounds of formula I may possess sensitive functional groups that require protecting groups when prepared with the intermediates described. Examples of suitable protecting groups may be found in T. W. Greene and P. Wuts, Protecting Groups in Organic Synthesis, John Wiley & Sons, 2nd Edition, New York, 1991.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Method for Assessing Biological Activities:

The activity of the compounds of the formula I of the present invention may be demonstrated by the following assays.

Human in vitro Assays

Human Cell-based COX-1 Assay

Human peripheral blood obtained from healthy volunteers can be diluted to ⅒ volume with 3.8% sodium citrate solution. The platelet-rich plasma immediately obtained can be washed with 0.14 M sodium chloride containing 12 mM Tris-HCl (pH 7.4) and 1.2 mM EDTA. Platelets can then be washed with platelet buffer (Hanks buffer (Ca free) containing 0.2% BSA and 20 mM Hepes). Finally, the human washed platelets (HWP) can be suspended in platelet buffer at the concentration of $2.85 \times 10^8$ cells/ml and stored at room temperature until use. The HWP suspension (70 μl aliquots, final $2.0 \times 10^7$ cells/ml) can be placed in a 96-well U bottom plate and 10 μl aliquots of 12.6 mM calcium chloride added. Platelets can be incubated with A23187 (final 10 μM, Sigma) with test compound (0.1–100 μM) dissolved in DMSO (final concentration; less than 0.01%) at 37° C. for 15 minutes. The reaction can be stopped by addition of EDTA (final 7.7 mM) and TxB2 in the supernatant quantitated by using a radioimmunoassay kit (Amersham) according to the manufacturer's procedure.

Human Cell-based COX-2 Assay

The human cell based COX-2 assay can be carried out as previously described (Moore et al., *Inflam. Res.*, 45, 54, 1996). Confluent human umbilical vein endothelial cells (HUVECs, Morinaga) in a 96-well flat bottom plate can be washed with 80 ml of RPMI1640 containing 2% FBS and incubated with hIL-1β (final concentration 300 U/ml, R & D Systems) at 37° C. for 24 hours. After washing, the activated HUVECs can be incubateed with test compound (final concentration; 0.1 nM-1 μM) dissolved in DMSO (final concentration; less than 0.01%) at 37° C. for 20 minutes and stimulated with A23187 (final concentration 30 mM) in Hanks buffer containing 0.2% BSA, 20 mM Hepes at 37° C. for 15 minutes. 6-Keto-PGF$_{1\alpha}$, stable metabolite of PGI2, in the supernatant can be quantitated by using a radioimmunoassay method (antibody; Preseptive Diagnostics, SPA; Amersham).

Canine in vitro Assays

The following canine cell based COX 1 and COX-2 assays have been reported in Ricketts et al., *Evaluation of Selective Inhibition of Canine Cyclooxygenase 1 and 2 by Carprofen and Other Nonsteroidal Anti-inflammatory Drugs*, American Journal of Veterinary Research, 59 (11), 1441–1446.

Protocol for Evaluation of Canine COX-1 Activity

Test drug compounds can be solubilized and diluted the day before the assay can be to be conducted with 0.1 mL of DMSO/9.9 mL of Hank's balanced salts solution (HBSS) and stored overnight at 4° C. On the day that the assay can be carried out, citrated blood can be drawn from a donor dog, centrifuged at 190×g for 25 minutes at room temperature and the resulting platelet-rich plasma can then be transferred to a new tube for further procedures. The platelets can be washed by centrifuging at 1500×g for 10 minutes at room temperature. The platelets can be washed with platelet buffer comprising Hank's buffer (Ca free) with 0.2% bovine serum albumin (BSA) and 20 mM HEPES. The platelet samples can then be adjusted to $1.5 \times 10^7$/mL, after which 50 μl of calcium ionophore (A23187) together with a calcium chloride solution can be added to 50 μl of test drug compound dilution in plates to produce final concentrations of 1.7 μM A23187 and 1.26 mM Ca. Then, 100 μl of canine washed platelets can be added and the samples can be incubated at 37° C. for 15 minutes, after which the reaction can be stopped by adding 20 μl of 77 mM EDTA. The plates can then be centrifuged at 2000×g for 10 minutes at 4° C., after which 50 μl of supernatant can be assayed for thromboxane B$_2$ (TXB$_2$) by enzyme-immunoassay (EIA). The pg/mL of TXB$_2$ can be calculated from the standard line included on each plate, from which it can be possible to calculate the percent inhibition of COX-1 and the IC$_{50}$ values for the test drug compounds.

Protocol for Evaluation of Canine COX-2 Activity

A canine histocytoma (macrophage-like) cell line from the American Type Culture Collection designated as DH82, can be used in setting up the protocol for evaluating the COX-2 inhibition activity of various test drug compounds. There can be added to flasks of these cells 10 μg/mL of LPS, after which the flask cultures can be incubated overnight. The same test drug compound dilutions as described above for the COX-1 protocol can be used for the COX-2 assay and can be prepared the day before the assay can be carried out. The cells can be harvested from the culture flasks by scraping and can then be washed with minimal Eagle's media (MEM) combined with 1% fetal bovine serum, centrifuged at 1500 rpm for 2 minutes and adjusted to a concentration of $3.2 \times 10^5$ cells/mL. To 50 μl of test drug dilution there can be added 50 μl of arachidonic acid in MEM to give a 10 μM final concentration and there can be added as well 100 μl of cell suspension to give a final concentration of $1.6 \times 10^5$ cells/mL. The test sample suspensions can be incubated for 1 hour and then centrifuged at 1000 rpm for 10 minutes at 4° C., after which 50 μl aliquots of each test drug sample can be delivered to EIA plates. The EIA can be performed for prostaglandin $E_2$ ($PGE_2$) and the pg/mL concentration of $PGE_2$ can be calculated from the standard line included on each plate. From this data it can be possible to calculate the percent inhibition of COX-2 and the $IC_{50}$ values for the test drug compounds. Repeated investigations of COX-1 and COX-2 inhibition can be conducted over the course of several months. The results are averaged and a single COX-1: COX-2 ratio is calculated.

Whole blood assays for COX-1 and COX-2 are known in the art such as the methods described in C. Brideau, et al., *A Human Whole Blood Assay for Clinical Evaluation of Biochemical Efficacy of Cyclooxygenase Inhibitors, Inflammation Research*, Vol. 45, pp. 68–74 (1996). These methods may be applied with feline, canine or human blood as needed.

In vivo Assays

Carrageenan Induced Foot Edema in Rats

Male Sprague-Dawley rats (5 weeks old, Charles River Japan) can be fasted overnight. A line can be drawn using a marker above the ankle on the right hind paw and the paw volume (V0) can be measured by water displacement using a plethysmometer (Muromachi). Animals can be given orally either vehicle (0.1% methyl cellulose or 5% Tween 80) or a test compound (2.5 ml per 100 g body weight). One hour later, the animals can then be injected intradermally with λ-carrageenan (0.1 ml of 1% w/v suspension in saline, Zushikagaku) into right hind paw (Winter et al., *Proc. Soc. Exp. Biol. Med.*, 111, 544, 1962; Lombardino et al., *Arzneim. Forsch.*, 25, 1629, 1975) and three hours later, the paw volume (V3) can be measured and the increase in volume (V3–V0) calculated. Since maximum inhibition attainable with classical NSAIDs is 60–70%, $ED_{30}$ values can be calculated.

Gastric Ulceration in Rats

The gastric ulcerogenicity of test compound can be assessed by a modification of the conventional method (Ezer et al., *J. Pharm. Pharmacol.*, 28, 655, 1976; Cashin et al., *J. Pharm. Pharmacol.*, 29, 330–336, 1977). Male Sprague-Dawley rats (5 weeks old, Charles River Japan), fasted overnight, can be given orally either vehicle (0.1% methyl cellulose or 5% Tween 80) or a test compound (1 ml per 10 g body weight). Six hours after, the animals can be sacrificed by cervical dislocation. The stomachs can be removed and inflated with 1% formalin solution (10 ml). Stomachs can be opened by cutting along the greater curvature. From the number of rats that showed at least one gastric ulcer or haemorrhaging erosion (including ecchymosis), the incidence of ulceration can be calculated. Animals did not have access to either food or water during the experiment.

Canine Whole Blood ex vivo Determinations of COX-1 and COX-2 Activity Inhibition The in vivo inhibitory potency of a test compound against COX-1 and COX-2 activity may be evaluated using an ex vivo procedure on canine whole blood. Three dogs can be dosed with 5 mg/kg of the test compound administered by oral gavage in 0.5% methylcellulose vehicle and three dogs can be untreated. A zero-hour blood sample can be collected from all dogs in the study prior to dosing, followed by 2- and 8-hour post-dose blood sample collections. Test tubes can be prepared containing 2 μL of either (A) calcium ionophore A23187 giving a 50 μM final concentration, which stimulates the production of thromboxane $B_2$ ($TXB_2$) for COX-1 activity determination; or of (B) lipopolysaccharide (LPS) to give a 10 μg/mL final concentration, which stimulates the production of prostaglandin $E_2$ ($PGE_2$) for COX-2 activity determination. Test tubes with unstimulated vehicle can be used as controls. A 500 μL sample of blood can be added to each of the above-described test tubes, after which they can be incubated at 37° C. for one hour in the case of the calcium ionophore-containing test tubes and overnight in the case of the LPS-containing test tubes. After incubation, 10 μL of EDTA can be added to give a final concentration of 0.3%, in order to prevent coagulation of the plasma which sometimes occurs after thawing frozen plasma samples. The incubated samples can be centrifuged at 4° C. and the resulting plasma sample of ~200 μL can be collected and stored at –20° C. in polypropylene 96-well plates. In order to determine endpoints for this study, enzyme immunoassay (EIA) kits available from Cayman can be used to measure production of $TXB_2$ and $PGE_2$, utilizing the principle of competitive binding of tracer to antibody and endpoint determination by calorimetry. Plasma samples can be diluted to approximate the range of standard amounts which would be supplied in a diagnostic or research tools kit, i.e., 1/500 for $TXB_2$ and 1/750 for $PGE_2$.

The data set out in Table 1 below show how the percent inhibition of COX-1 and COX-2 activity is calculated based on their zero hour values. The data is expressed as treatment group averages in pg/ml of $TXB_2$ and $PGE_2$ produced per sample. Plasma dilution can be not factored in said data values.

The data in Table 1 show that, in this illustration, at the 5 mg/kg dose there can be significant COX-2 inhibition at both timepoints. The data in Table 1 also show that at the 5 mg/kg dose there can be no significant inhibition of COX-1 activity at the timepoints involved. Accordingly, the data in Table 1 clearly demonstrates that at the 5 mg/kg dosage concentration this compound possesses good COX-2 selectivity.

TABLE 1

| COX-1 ACTIVITY INHIBITION—Group Averages | | | | | |
|---|---|---|---|---|---|
| | $TXB_2$ Pg/mL/Well | | | Percent Inhibition | |
| Hour | 0-hour | 2-hour | 8-hour | 2-hour | 8-hour |
| Untreated | 46 | 45 | 140 | 2% | 0% |
| 5 mg/kg | 41 | 38 | 104 | 7% | 0% |

| COX-2 ACTIVITY INHIBITION—Group Averages | | | | | |
|---|---|---|---|---|---|
| | $PGE_2$ Pg/mL/Well | | | Percent Inhibition | |
| Hour | 0-hour | 2-hour | 8-hour | 2-hour | 8-hour |
| Untreated | 420 | 486 | 501 | 0% | 0% |
| 5 mg/kg | 711 | 165 | 350 | 77% | 51% |

COX inhibition is observed when the measured percent inhibition is greater than that measured for untreated controls. The percent inhibition in the above table is calculated in a straightforward manner in accordance with the following equation:

$$\% \text{ Inhibition}(2\text{-hour}) = \frac{(PGE_2 \text{ at } t = 0) - (PGE_2 \text{ at } t = 2)}{(PGE_2 \text{ at } t = 0)}$$

Data Analysis

Statistical program packages, SYSTAT (SYSTAT, INC.) and StatView (Abacus Cencepts, Inc.) for Macintosh can be used. Differences between test compound treated group and control group can be tested for using ANOVA. The $IC_{50}$ (ED30) values can be calculated from the equation for the log-linear regression line of concentration (dose) versus percent inhibition.

Most compounds prepared in the Working Examples as described hereinafter can be tested by at least one of the methods described above and showed $IC_{50}$ values of 0.001 $\mu$M to 3 $\mu$M with respect to inhibition of COX-2 in either the canine or human assays.

COX-2 selectivity can be determined by ratio in terms of $IC_{50}$ value of COX-1 inhibition to COX-2 inhibition. In general, it can be said that a compound showing a COX-1/COX-2 inhibition ratio of more than 5 has good COX-2 selectivity.

The compounds of the formula I of this invention can be administered via oral, parenteral, anal, buccal or topical routes to mammals (including humans, dogs, cats, horses and livestock).

In general, these compounds are most desirably administered to humans in doses ranging from 0.01 mg to 100 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of abovementioned diseases.

These compounds are most desirably administered to said non-human mammals, e.g. dogs, cats, horses or livestock in an amount, expressed as mg per kg of body weight of said member per day, ranging from about 0.01 mg/kg to about 20.0 mg/kg/day, preferably from about 0.1 mg/kg to about 12.0 mg/kg/day, more preferably from about 0.5 mg/kg to about 10.0 mg/kg/day and most preferably from about 0.5 mg/kg to about 8.0 mg/kg/day.

The compounds of the present invention may be administered alone or in combination with pharmaceutically acceptable carriers or diluents by either of the above routes previously indicated and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging from 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes and, if so desired, emulsifying and/or suspending agents as well, together with such diluents as water, ethanol, propylene glycol, glycerin and various combinations thereof.

A preferred composition for dogs comprises an ingestible liquid peroral dosage form selected from the group consisting of a solution, suspension, emulsion, inverse emulsion, elixir, extract, tincture and concentrate, optionally to be added to the drinking water of the dog being treated. Any of these liquid dosage forms, when formulated in accordance with methods well known in the art, can either be administered directly to the dog being treated, or may be added to the drinking water of the dog being treated. The concentrate liquid form, on the other hand, is formulated to be added first to a given amount of water, from which an aliquot amount may be withdrawn for administration directly to the dog or addition to the drinking water of the dog.

A preferred composition provides delayed-, sustained- and/or controlled-release of said anti-inflammatory selective COX-2 inhibitor. Such preferred compositions include all such dosage forms which produce $\geq 80\%$ inhibition of COX-2 isozyme activity and result in a plasma concentration of said inhibitor of at least 3 fold the COX-2 $IC_{50}$ for at least 4 hours; preferably for at least 8 hours; more preferably for at least 12 hours; more preferably still for at least 16 hours; even more preferably still for at least 20 hours; and most preferably for at least 24 hours. Preferably, there is included within the above-described dosage forms those which produce $\geq 80\%$ inhibition of COX-2 isozyme activity and result in a plasma concentration of said inhibitor of at least 5 fold the COX-2 $IC_{50}$ for at least 4 hours, preferably for at least 8 hours, more preferably for at least 12 hours, still more preferably for at least 20 hours and most preferably for at least 24 hours. More preferably, there is included the above-described dosage forms which produce $\geq 90\%$ inhibition of COX-2 isozyme activity and result in a plasma concentration of said inhibitor of at least 5 fold the COX-2 $IC_{50}$ for at least 4 hours, preferably for at least 8 hours, more preferably for at least 12 hours, still more preferably for at least 20 hours and most preferably for at least 24 hours.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of formula I may also be administered in the form of suppositories for rectal or vaginal administration of the active ingredient. These compositions can be prepared by mixing the active ingredient with a suitable non-irritating excipient which is solid at room temperature (for example, 10° C. to 32° C.) but liquid at the rectal temperature and will melt in the rectum or vagina to release the active ingredient. Such materials are polyethylene glycols, cocoa butter, suppository and wax.

For buccal administration, the composition may take the form of tablets or lozenges formulated in conventional manner.

For transdermal administration, transdermal patches prepared in accordance with well known drug delivery technology may be prepared and applied to the skin of a mammal, preferably a human or a dog, to be treated, whereafter the active agent by reason of its formulated solubility characteristics migrates across the epidermis and into the dermal layers of the skin where it is taken up as part of the general circulation, ultimately providing systemic distribution of the active ingredient over a desired, extended period of time. Also included are implants which are placed beneath the epidermal layer of the skin, i.e. between the epidermis and the dermis of the skin of the patient being treated. Such an implant will be formulated in accordance with well known principles and materials commonly used in this delivery technology and may be prepared in such a way as to provide controlled-, sustained- and/or delayed-release of the active ingredient into the systemic circulation of the patient. Such subepidermal (subcuticular) implants provide the same facility of installation and delivery efficiency as transdermal patches, but without the limitation of being subject to degradation, damage or accidental removal as a consequence of being exposed on the top layer of the patient's skin.

EXAMPLES

The following examples contain detailed descriptions of the methods of the preparation of compounds of formula I. These detailed descriptions fall within the scope of the invention and serve to exemplify the above described general synthetic procedures which form part of the invention. These detailed descriptions are presented for illustrative purposes only and are not intended to restrict the scope of the present invention.

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath of up to 60° C.; reactions were monitored by thin layer chromatography (TLC) and analytical column liquid chromatography and reaction times are given for illustration only; melting points (m.p.) given are uncorrected (polymorphism may result in different melting points); structure and purity of all isolated compounds were assured by at least one of the following techniques: TLC (Merck silica gel 60 F-254 precoated plates), high performance liquid chromatogrpay (HPLC), or mass spectrometry. Flash column chromatography was carried out using Merck silica gel 60 (230–400 mesh ASTM). Preparative HPLC was carried out using Hewlett Packard 1100 Liquid Chromatography/Mass Selective Detector (LC/MSD). Separation was done on a Monochrom 5$\mu$ CN column PN 0509-250*212 from MetaChem Technologies. The flow rate was 20 ml/min running a gradient of 0 to 90% of isopropanol in n-hexane. Low-resolution mass spectral data (EI) were obtained on an Automass 120 (JEOL) mass spectrometer. Liquid Chromatography data was collected on a Hewlett Packard 1100 Liquid Chromatography/Mass Selective Detector (LC/MSD). Analysis was performed on a Luna C-18 column with dimensions of 3.0×150 mm. The flow rate was 0.425 ml/minute running a gradient of 50% 0.1% aqueous formic acid and 50% acetonitrile to 100% acetonitrile in 15 minutes. The ionization type for the mass detector of the Mass Spectrophotometer was atmospheric pressure electrospray in the positive ion mode with a fragmentor voltage of 50 volts.

Example 1

6-[4-Cyano-5-(2,2-dimethyl-propylamino)-3-trifluoromethyl-pyrazol-1-yl]-pyridine-3-sulfonic Acid acetyl-amide Sodium Salt 6-[4-Cyano-5-(2,2-dimethyl-propylamino)-3-trifluoromethyl-pyrazol-1-yl]-pyridine-3-sulfonic acid amide (166.3 mg, 0.413 mMol), was dissolved in methylene chloride (10 ml) and stirred under nitrogen. Acetic anhydride (126.5 mg, 1.239 mMol), triethylamine (49.3 mg, 0.49 mMol) and N,N-dimethylaminopyridine (25.2 mg, 0.5 mMol) were added into the methylene chloride solution, and stirred for 18 hours. The reaction mixture was washed with water and brine, dried with magnesium sulfate, filtered, and evaporated. The residue was chromatographed on silica, eluting with 0.75% methanol/methylene chloride, to give a free acid in 80% yield. The free acid was converted to the sodium salt by reacting the free acid with one equivalent of sodium hydroxide in ethanol, evaporation, and drying under high vacuum. The desired product was isolated by chromatography on silica gel column. MS: 443.5 ES, r.t.: 3.0 minutes.

Example 2

6-[4-Cyano-5-(2,2-dimethyl-propylamino)-3-trifluoromethyl-pyrazol-1-yl]-pyridine-3-sulfonic Acid propionyl-amide Sodium Salt 6-[4-Cyano-5-(2,2-dimethyl-propylamino)-3-trifluoromethyl-pyrazol-1-yl]-pyridine-3-sulfonic acid amide (166.3 mg, 0.413 mMol), was dissolved in methylene chloride (10 ml) and stirred under nitrogen. Propionic anhydride (161.24 mg, 1.239 mMol), triethylamine (49.3 mg, 0.49 mMol) and N,N-dimethylaminopyridine (25.2 mg, 0.5 mMol) were added into the methylene chloride solution, and stirred for 18 hours. The reaction mixture was washed with water and brine, dried with magnesium sulfate, filtered, and evaporated. The residue was chromatographed on silica, eluting with 0.75% methanol/methylene chloride, to give a free acid in 80% yield. The free acid was converted to the sodium salt by reacting the free acid with one equivalent of sodium hydroxide in ethanol, evaporation, and drying under high vacuum. The desired product was isolated by chromatography on silica gel column. MS: 457.6 ES, r.t.: 3.1 min.

The following compounds summarized in the following Table 2 may be prepared according to the procedure described in the above Examples 1 and 2 by using appropriate starting materials.

TABLE 2

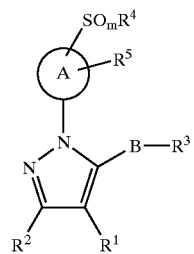

| Ex.# | A | m | $R^1$ | $R^2$ | $R^4$ | $R^5$ | $B-R^3$ |
|---|---|---|---|---|---|---|---|
| 1 | A2, wherein X is >CH | 2 | —CN | —CF$_3$ | —NH—(C=O)—CH$_3$ | H | —N—CH$_2$—C(CH$_3$)$_3$ |
| 2 | A2, wherein X is >CH | 2 | —CN | —CF$_3$ | —NH—(C=O)—CH$_2$CH$_3$ | H | —N—CH$_2$—C(CH$_3$)$_3$ |
| 3 | A2, wherein X is >CH | 2 | —CN | —CF$_3$ | —NH—(C=O)—CH(CH$_3$)$_2$ | —H | —N—CH$_2$—C(CH$_3$)$_3$ |
| 4 | A2, wherein X is >CH | 2 | —CN | —CF$_3$ | —NH—(C=O)—CH(CH$_3$)$_2$ | —H | —N—CH$_2$—C(CH$_3$)$_3$ |
| 5 | A2, wherein X is >CH | 2 | —CN | —CF$_3$ | —NH—(C=O)—O—CH(CH$_3$)$_2$ | —H | —N—CH$_2$—C(CH$_3$)$_3$ |
| 6 | A2, wherein X is >CH | 2 | —CN | —CF$_3$ | —NH—(C=O)—CH(CH$_3$)—CH$_2$CH$_3$ | —H | —N—CH$_2$—C(CH$_3$)$_3$ |
| 7 | A2, wherein X is >CH | 2 | —CN | —CF$_3$ | —NH—(C=O)—CH$_3$ | —H | —O—CH$_2$-(cyclopentyl) |
| 8 | A2, wherein X is >CH | 2 | —CN | —CF$_3$ | —NH—(C=O)—CH$_2$CH$_3$ | —H | —O—CH$_2$-(cyclopentyl) |
| 9 | A2, wherein X is >CH | 2 | —CN | —CF$_3$ | —NH—(C=O)—CH(CH$_3$)$_2$ | —H | —O—CH$_2$-(cyclopentyl) |
| 10 | A2, wherein X is >CH | 2 | —CN | —CF$_3$ | —NH—(C=O)—O—CH(CH$_3$)$_2$ | —H | —O—CH$_2$—C(CH$_3$)$_3$ |
| 11 | A2, wherein X is >CH | 2 | —CN | —CF$_3$ | —NH—(C=O)—CH(CH$_3$)—CH$_2$CH$_3$ | —H | —O—CH$_2$—C(CH$_3$)$_3$ |
| 12 | A2, wherein X is >CH | 2 | —CN | —CF$_3$ | —NH—(C=O)—CH$_3$ | —H | —O—CH$_2$—C(CH$_3$)$_3$ |
| 13 | A2, wherein X is >CH | 2 | —CN | —CF$_3$ | —NH—(C=O)—CH$_2$CH$_3$ | —H | —O-(3-(CH$_3$)-cyclohexyl) |
| 14 | A2, wherein X is >CH | 2 | —CN | —CF$_3$ | —NH—(C=O)—CH(CH$_3$)$_2$ | —H | —O-(3-(CH$_3$)-cyclohexyl) |
| 15 | A2, wherein X is >CH | 2 | —CN | —CF$_3$ | —NH—(C=O)—O—CH(CH$_3$)$_2$ | —H | —O-(3-(CH$_3$)-cyclohexyl) |
| 16 | A2, wherein X is >CH | 2 | —CN | —CF$_3$ | —NH—(C=O)—CH$_3$ | —H | —SO$_2$—CH(CH$_3$)—CH$_2$CH$_3$ |
| 17 | A2, wherein X is >CH | 2 | —CN | —CF$_3$ | —NH—(C=O)—CH(CH$_3$)—CH$_2$CH$_3$ | —H | —SO$_2$—CH(CH$_3$)—CH$_2$CH$_3$ |
| 18 | A2, wherein X is >CH | 2 | —CN | —CF$_3$ | —NH—(C=O)—O—CH(CH$_3$)$_2$ | —H | —SO$_2$—CH(CH$_3$)—CH$_2$CH$_3$ |
| 19 | A2, wherein X is >CH | 2 | —CN | —CHF$_2$ | —NH—(C=O)—CH$_3$ | —H | —SO$_2$—CH(CH$_3$)—CH$_2$CH$_3$ |
| 20 | A2, wherein X is >CH | 2 | —CN | —CHF$_2$ | —NH—(C=O)—CH$_2$CH$_3$ | —H | —SO$_2$—CH(CH$_3$)—CH$_2$CH$_3$ |
| 21 | A2, wherein X is >CH | 2 | —CN | —CHF$_2$ | —NH—(C=O)—CH(CH$_3$)$_2$ | —H | —SO$_2$—CH(CH$_3$)—CH$_2$CH$_3$ |
| 22 | A2, wherein X is >CH | 2 | —CN | —CF$_3$ | —N=CH—N(CH$_3$)$_2$ | —H | —O—CH$_2$-(cyclobutyl) |
| 23 | A2, wherein X is >CH | 2 | —CN | —CF$_3$ | —N—CH$_2$CH$_3$ | —H | —N—CH$_2$—C(CH$_3$)$_3$ |
| 24 | A2, wherein X is >CH | 2 | —CN | —CF$_3$ | —N—CH$_2$-(cyclopropyl) | —H | —N—CH$_2$-(tetrahydrofuran-2-yl) |

Referring to Table 2, Ex.#. refers to Example number.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:

1. A compound of the formula I:

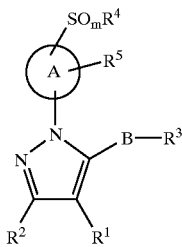

I or a pharmaceutically acceptable salt thereof;
wherein the ring of the formula $(R^5)$-A-$(SO_mR^4)$ is selected from the group consisting of

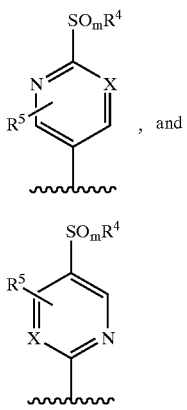

A1

, and

A2 m is 2;
X is $CR^5$;
$R^1$ is a radical selected from the group consisting of H, $-NO_2$, $-CN$, $H-(C=O)-$, $(C_1-C_8)$alkyl-$(C=O)-$;
$R^2$ is a radical selected from the group consisting of H, and $(C_1-C_6)$alkyl optionally substituted by one to four fluoro substituents;
B is $-O-$, $-S-$, $-SO-$, $-SO_2-$ or $R^6-N-$;
$R^3$ is a radical selected from the group consisting of $(C_1-C_6)$alkyl, $(C_3-C_{10})$cycloalkyl and $(C_1-C_9)$ heterocyclyl;
wherein each of said $R^3$ $(C_1-C_6)$alkyl, $(C_3-C_{10})$ cycloalkyl, or $(C_1-C_9)$heterocyclyl radicals may optionally be substituted with one to three substituents independently selected from the group consisting of $(C_1-C_6)$alkyl, and $(C_3-C_{10})$cycloalkyl;
$R^4$ is a radical selected from the group consisting of $(C_1-C_8)$alkyl-NH—, [$(C_1-C_6)$alkyl]$_2$—N—, [$C_3-C_7$) cycloalkyl-NH—, $(C_1-C_6)$alkyl-$(C=O)$—NH—, $(C_3-C_7)$cycloalkyl-$(C=O)$—HN—, $(C_1-C_6)$alkyl-NH—HC=N—, $(C_1-C_6)$alkyl]$_2$N—HC=N—, and cylcopropyl-CH2—NH—;
$R^6$ is a radical selected from the group consisting of H; and
$R^6$ is a radical selected from the group consisting of H.

2. The compound according to claim 1 wherein $R^4$ is a radical selected from the group consisting of $(C_1-C_6)$alkyl-NH— and $(C_3-C_7)$cycloalkyl-NH—.

3. The compound according to claim 1 wherein $R^4$ is a radical selected from the group consisting of $(C_1-C_6)$alkyl-$(C=O)$—NH—.

4. The compound according to claim 1 wherein $R^4$ is a radical selected from the group consisting of [$(C_1-C_6)$alkyl]-NH—HC=N—, and [$C_1-C_6$)alkyl]$_2$N—HC=N—.

5. The compound according to claim 1 wherein $R^4$ is a radical selected from the group consisting of $(C_1-C_6)$alkyl-$(C=O)$—NH—, $(C_1-C_6)$alkyl-NH—, and [$(C_1-C_6)$alkyl]-NH—HC=N—.

6. The compound according to claim 1 wherein B is —O—.

7. The compound according to claim 1 wherein B is —SO$_2$—.

8. The compound according to claim 1 wherein B is $R^6$—N—.

9. The compound according to claim 1 wherein $R^3$ is a radical selected front the group consisting of $(C_1-C_6)$alkyl, and $(C_3-C_{10})$cycloalkyl.

10. The compound according to claim 1 wherein $R^1$ is a radical selected from the group consisting of —CN.

11. A compound according to claim 1 wherein said compound is selected from the group consisting of:

6-[4-Cyano-5-(2,2-dimethyl-propylamino)-3-trifluoromethyl-pyrazol-1-yl]-pyridine-3-sulfonic acid acetyl-amide;

6-[4-Cyano-5-(2,2-dimethyl-propylamino)-3-trifluoromethyl-pyrazol-1-yl]-pyridine-3-sulfonic acid propionyl-amide;

6-[4-Cyano-5-(2,2-dimethyl-propylamino)-3-trifluoromethyl-pyrazol-1-yl]-pyridine-3-sulfonic acid isobutyryl-amide;

6-[4-Cyano-5-(2,2-dimethyl-propylamino)-3-trifluoromethyl-pyrazol-1-yl]-pyridine-3-sulfonic acid (2,2-dimethyl-propionyl)-amide;

6-[4-Cyano-5-(2,2-dimethyl-propylamino)-3-trifluoromethyl-pyrazol-1-yl]-pyridine-3-sulfonic acid (1,1-dimethyl)-ethoxy-amide;

6-[4-Cyano-5-(2,2-dimethyl-propylamino)-3-trifluoromethyl-pyrazol-1-yl]-pyridine-3-sulfonic acid (3-methyl-butyryl)-amide;

6-(4-Cyano-5-cyclopentylmethoxy-3-trifluoromethyl-pyrazol-1-yl)-pyridine-3-sulfonic acid acetyl amide;

6-(4-Cyano-5-cyclopentylmethoxy-3-trifluoromethyl-pyrazol-1-yl)-pyridine-3-sulfonic acid proplonyl amide;

6-(4-Cyano-5-cyclopentylmethoxy-3-trifluoromethyl-pyrazol-1-yl)-pyridine-3-sulfonic acid isobutryl amide;

6-[4-Cyano-5-(2,2-dimethyl-propoxy)-3-trifluoromethyl-pyrazol-1-yl]-pyridine-3-sulfonic acid (1,1-dimethylethoxy)amide;

6-[4-Cyano-5-(2,2-dimethyl-propoxy)-3-trifluoromethyl-pyrazol-1-yl]-pyridine-3-sulfonic acid (3-methyl-butyryl) amide;

6-[4-Cyano-5-(2,2-dimethyl-propoxy)-3-trifluoromethyl-pyrazol-1-yl]-pyridine-3-sulfonic acid acetyl amide;

6-[4-Cyano-5-(3-methyl-cyclohexyloxy)-3-trifluoromethyl-pyrazol-1-yl]-pyridine-3-sulfonic acid propionyl amide;

6-[4-Cyano-5-(3-methyl-cyclohexyloxy)-3-trifluoromethyl-pyrazol-1-yl]-pyridine-3-sulfonic acid isobutyryl amide;

6-[4-Cyano-5-(3-methyl-cyclohexyloxy)-3-trifluoromethyl-pyrazol-1-yl]-pyridine-3-sulfonic acid (1,1-dimethylethoxy) amide;

6-(5-sec-Butylsulfanyl-4-cyano-3-trifluoromethyl-pyrazol-1-yl)-pyridine-3-sulfonic acid acetyl amide;

6-(5-sec-Butylsulfanyl-4-cyano-3-trifluoromethyl-pyrazol-1-yl)-pyridine-3-sulfonic acid (3-methyl-butyryl)amide;

6-(5-sec-Butylsulfanyl-4-cyano-3-trifluoromethyl-pyrazol-1-yl)-pyridine-3-sulfonic acid (1,1-dimethylethoxy)amide;

6-(5-sec-Butylsulfanyl-4-cyano-3-difluoromethyl-pyrazol-1-yl)-pyridine-3-sulfonic acid acetyl amide;

6-(5-sec-Butylsulfanyl-4-cyano-3-difluoromethyl-pyrazol-1-yl)-pyridine-3-sulfonic acid propionyl amide; and 6-(5-sec-Butylsulfanyl-4-cyano-3-difluoromethyl-pyrazol-1-yl)-pyridine-3-sulfonic acid isobutyryl amide; or a pharmaceutically acceptable salt thereof.

12. A pharmaceutical composition for the treatment of a condition selected from the group consisting of arthritis, in a mammal, comprising an amount of a compound of claim 1 or a pharmaceutically acceptable salt thereof effective in such treatments and a pharmaceutically acceptable carrier.

13. A method for treating a condition selected from the group consisting of arthritis, in a mammal, comprising administering to said mammal an amount of a compound according to claim 1 or a pharmaceutically acceptable salt thereof effective in treating such a condition.

* * * * *